United States Patent
Kissel et al.

(10) Patent No.: US 10,471,058 B2
(45) Date of Patent: Nov. 12, 2019

(54) PHARMACEUTICAL FORMULATIONS AND THEIR USE IN THE TREATMENT OF PERIODONTAL DISEASE

(71) Applicant: PERIOC LTD, Ongar (GB)

(72) Inventors: Thomas Kissel, Staufen (DE); Ching Pong Mak, Therwil (CH)

(73) Assignee: PERIOC LTD, Ongar (GB)

( * ) Notice: Subject to any disclaimer, the term of this patent is extended or adjusted under 35 U.S.C. 154(b) by 0 days.

(21) Appl. No.: 14/651,165

(22) PCT Filed: Dec. 13, 2013

(86) PCT No.: PCT/GB2013/053283
§ 371 (c)(1),
(2) Date: Jun. 10, 2015

(87) PCT Pub. No.: WO2014/091239
PCT Pub. Date: Jun. 19, 2014

(65) Prior Publication Data
US 2015/0313959 A1 Nov. 5, 2015

(30) Foreign Application Priority Data
Dec. 13, 2012 (GB) .................................. 1222455.6

(51) Int. Cl.
| | | |
|---|---|---|
| *A61K 38/13* | (2006.01) | |
| *A61K 9/14* | (2006.01) | |
| *A61K 31/5025* | (2006.01) | |
| *A61K 9/10* | (2006.01) | |
| *A61K 47/34* | (2017.01) | |
| *C07K 7/64* | (2006.01) | |
| *A61K 38/15* | (2006.01) | |
| *A61K 47/10* | (2017.01) | |
| *A61K 47/22* | (2006.01) | |
| *A61K 31/155* | (2006.01) | |
| *A61K 9/00* | (2006.01) | |

(52) U.S. Cl.
CPC ........ *A61K 31/5025* (2013.01); *A61K 9/0063* (2013.01); *A61K 9/10* (2013.01); *A61K 9/145* (2013.01); *A61K 31/155* (2013.01); *A61K 38/13* (2013.01); *A61K 38/15* (2013.01); *A61K 47/10* (2013.01); *A61K 47/22* (2013.01); *A61K 47/34* (2013.01); *C07K 7/645* (2013.01)

(58) Field of Classification Search
None
See application file for complete search history.

(56) References Cited

U.S. PATENT DOCUMENTS

| | | | | | |
|---|---|---|---|---|---|
| 5,565,188 | A | * | 10/1996 | Wong | A61K 9/146 424/489 |
| 5,886,030 | A | * | 3/1999 | Maniar | A61K 9/0048 514/458 |
| 5,891,845 | A | * | 4/1999 | Myers | A61K 9/1274 424/451 |
| 8,772,245 | B2 | * | 7/2014 | Gore | C07K 7/645 514/20.5 |
| 9,572,859 | B2 | * | 2/2017 | Hughes | A61K 9/0048 |
| 2005/0277584 | A1 | * | 12/2005 | Tien | A61K 9/0048 514/20.8 |
| 2008/0274194 | A1 | * | 11/2008 | Miller | A61K 9/146 424/489 |
| 2008/0299206 | A1 | * | 12/2008 | Lee | A61K 9/0048 424/489 |
| 2009/0215731 | A1 | * | 8/2009 | Birrell | A61K 31/4196 514/170 |
| 2011/0064800 | A1 | * | 3/2011 | Jenkins | A61K 31/395 424/452 |
| 2011/0142945 | A1 | * | 6/2011 | Chen | A61K 9/4858 424/489 |
| 2011/0200678 | A1 | * | 8/2011 | Hwang | B01J 2/04 424/489 |

FOREIGN PATENT DOCUMENTS

| | | | |
|---|---|---|---|
| CN | 1571794 | A | 1/2005 |
| CN | 101032620 | A | 9/2007 |
| CN | 101048137 | A | 10/2007 |
| CN | 102085295 | A | 6/2011 |
| DE | 19932157 | A1 | 1/2001 |
| JP | H0597697 | A | 4/1993 |
| WO | WO-03033527 | A2 * | 4/2003 ........... A61K 9/0095 |
| WO | 2009/083155 | A1 | 7/2009 |

OTHER PUBLICATIONS

Ke et al., J. Contr. Rel. 102:489-507 (2005).*
Ghosal et al., Der Pharmacia Sinica 2:152-168 (2011).*
Hosseinzadeh et al., Intl. J. Nanomed. 7:1851-1863 (2012).*
BASF, Technical Bulletin: Pluronic® Block Copolymers NF Grade (Poloxamer NF Grades), 2 pages (2004).*
http://www.edinformatics.com/math_science/suspensions_colloids. htm, 2 pages, (accessed on Dec. 7, 2016).*
Nakarani et al., Sci. Pharm. 78:345-361 (2010) (Year: 2010).*
Wandrey et al., "Chapter 3: Materials for Encapsulation," in Encapsulation Technologies for Active Food Ingredients and Food Processing, Zuidam et al., eds., pp. 31-34, 41-46, 61-67, 72-75, and 79-100 (2010) (Year: 2010).*
Robin, PharmTech.com 39:1-5 (2015) (Year: 2015).*
Chang et al., Clin. Pharmacol. & Ther. 59:297-303 (1996) (Year: 1996).*

(Continued)

*Primary Examiner* — James H Alstrum-Acevedo
*Assistant Examiner* — Thea D' Ambrosio
(74) *Attorney, Agent, or Firm* — McCarter & English, LLP; Steven G. Davis; Mei Bai

(57) ABSTRACT

The present invention relates to novel treatments of periodontal disease by administering a suitable formulation of a cyclophilin inhibitor. The present invention further relates to novel pharmaceutical compositions containing said cyclophilin inhibitor compounds.

16 Claims, 5 Drawing Sheets

(56) References Cited

OTHER PUBLICATIONS

BASF, The Chemical Company, "Solubility Enhancement with BASF Pharma Polymers, Solubilizer Compendium," BASF SE, Pharma Ingredients & Services, pp. 1-130 (2011) (Year: 2011).*
Constantinides et al., Pharma. Res. 23:243-255 (2006) (Year: 2006).*
Ghosal et al., "Hydroxypropyl methylcellulose in drug delivery" Der Pharmacia Sinica, 2(2):152-168, 2011.
International Search Report and Written Opinion issued in PCT/GB2013/053283 dated Feb. 14, 2014.
Kim et al., "A Novel Mucoadhesive Polymer Film Composed of Carbopol, Poloxamer and Hydroxypropylmethylcellulose" Arch. Pharm. Res., vol. 30(3): 381-386, 2007.

* cited by examiner

| Batch No. | G0637N016 |
|---|---|
| API [%] | 5.00 |
| TPGS [%] | 1.00 |
| Poloxamer 407 [%] | 1.00 |
| H$_2$O [%] | 93.00 |

| PSD G0637N016 | Medium | d (0.1) [nm] | d (0.5) [nm] | d (0.9) [nm] | Assay [%] |
|---|---|---|---|---|---|
| before | water | 1,192 | 2,047 | 3,810 | - |
| initial | water | 84 | 135 | 523 | 88.7 |
| 2 weeks (2-8°C) | water | 83 | 135 | 556 | - |
| 2 weeks (25°C) | water | 81 | 135 | 615 | - |
| 4 weeks (2-8°C) | water | 85 | 136 | 526 | - |
| 4 weeks (25°C) | water | 80 | 133 | 615 | - |
| 8 weeks (2-8°C) | water | 80 | 133 | 514 | 87.8 |
| 8 weeks (25°C) | water | 75 | 129 | 639 | 88.8 |
| 8 weeks (2-8°C) | water | 80 | 134 | 524 | - |

| Batch No. | G0637N017 |
|---|---|
| API [%] | 5.00 |
| Sodium Glycocholate [%] | 0.80 |
| Poloxamer 407 [%] | 2.00 |
| H$_2$O [%] | 92.50 |

| PSD G0637N017 | Medium | d (0.1) [nm] | d (0.5) [nm] | d (0.9) [nm] | Assay [%] |
|---|---|---|---|---|---|
| before | water | 1,361 | 2,766 | 19,344 | - |
| initial | water | 86 | 138 | 506 | 94.3 |
| 2 weeks (2-8°C) | water | 86 | 137 | 272 | - |
| 2 weeks (25°C) | water | 85 | 136 | 617 | - |
| 4 weeks (2-8°C) | water | 85 | 136 | 276 | - |
| 4 weeks (25°C) | water | 85 | 136 | 613 | - |
| 8 weeks (2-8°C) | water | 83 | 133 | 548 | 95.2 |
| 8 weeks (25°C) | water | 100 | 568 | 23,652 | 92.2 |

PHARMACEUTICAL FORMULATIONS AND THEIR USE IN THE TREATMENT OF PERIODONTAL DISEASE

CROSS-REFERENCE TO RELATED APPLICATIONS

This application is a 35 U.S.C. § 371 national stage filing of International Application No. PCT/GB2013/053283, filed on Dec. 13, 2013, which claims the benefit of United Kingdom Patent Application No. 1222455.6, filed on Dec. 13, 2012. Each of the foregoing applications is incorporated herein by reference in its entirety.

FIELD OF THE INVENTION

The present invention relates to a new treatment of periodontal disease by administering a suitable topical formulation of a cyclophilin inhibitor into the gingival pockets. The method includes a new in-situ formulation and use of compounds. Further disclosed is a micro-formulation or nano-formulation of stabilised micro or nanoparticles. The novel nanoparticles may also be used in the treatment of periodontal disease. The formulation can be an in-situ forming system which is applied as a liquid, but forms a gel under physiological conditions.

BACKGROUND OF THE INVENTION

Periodontal diseases range from simple gum inflammation to serious disease that results in major damage to the soft tissue and bone that surround and support the teeth, ultimately resulting in tooth loss. The diseases are caused by bacterial colonization of the tooth surface, followed initially by a response of the innate immune system and manifest as gum inflammation (gingivitis). This gum inflammation then progresses to become periodontitis, in which the gums pull away from the teeth and form pockets in which the infection further thrives.

The innate immune response is followed by an adaptive immune response, in which antigen-presenting cells (mainly dendritic cells) accumulate in the gingiva and orchestrate a T cell response which in turn activates B cells to produce specific antibodies. CD4+ T cells have been shown to be the predominant population in adult periodontitis and, via recruitment and activation of osteoclasts function as a major source of bone loss. Thus, periodontal disease, while initially triggered by infection, is essentially an immunopathology, in which it is the immune response ensuing the infection that is responsible for the damage to tissue and bone.

Presently, the treatment of periodontal diseases consists primarily in eliminating the infection, mainly by mechanical removal of the plaque by scaling, debridement and root planing. The mechanical treatment can be supported by antimicrobial measures, such as mouth rinses or locally applied gels containing an antiseptic such as chlorhexidine. Tetracycline antibiotics (doxycycline, minocycline) are also used to combat the infection, either in form of locally applied preparations or in form of tablets. Tetracyclines act not only as antimicrobials but have in addition anti-inflammatory properties, which are poorly understood. Both minocycline and doxycycline have been shown to inhibit the release and the activity of matrix metallo proteinases (MMPs), a large group of enzymes that can be released from a variety of cells and are the main culprits of degrading tissue, cartilage and bone in many chronic inflammatory diseases, including periodontitis.

There is presently no treatment that addresses the events of the inflammatory response in a comprehensive way, notably its chronic manifestations, such that it would halt or reverse the tissue and bone destructive process. The drug compositions subject of this invention represent such a treatment.

Role of Cyclophilin in the Inflammatory Process

Cyclophilin was first discovered as binding protein of the immunosuppressant cyclosporin, normally resident within cells. The re-discovery of cyclophilin as intracellular peptidyl-prolyl cis-trans isomerase (PPIase) was reported several years later. Exposure of cells to inflammatory stimuli such as bacterial cell wall components (e.g. lipopolysaccharide, LPS) triggers cyclophilin to be secreted from cells into the extracellular space where it acts as a chemoattractant for inflammatory leukocytes. Leukocyte chemotaxis is mediated by a widely expressed membrane glycoprotein called CD147 or EMMPRIN (Extracellular Matrix Metallo Proteinase INducer) due to its ability to induce the production and release of MMPs from these cells. Both MMP release as well as leukocyte chemotaxis are triggered by the interaction between CD147 and cyclophilin, which occurs via the PPIase catalytic site which is also the cyclosporin binding site. Cyclosporin and other compounds that inhibit the PPIase catalytic activity of cyclophilin therefore block several key events involved in the bone and tissue destructive process of periodontal disease:

(1) They inhibit the infiltration of inflammatory leukocytes
(2) they inhibit the formation of antibody-secreting plasma cells resident in the gingiva
(3) they prevent the production and release of matrix metallo proteinases.

Cyclophilin inhibitors therefore represent a novel modality to treat the underlying mechanisms causing the immunopathology of periodontal disease.

Cyclosporin, when administered subcutaneously, has a positive effect on the formation of new alveolar bone (Toxicologic Pathology, Vol. 34(6), 2006, (Cetinkaya, Burcu Ozkan et al), "The effect of cyclosporin A on alveolar bone in rats subjected to experimental periodontal disease", pages 716-722). The cyclosporin is administered as a subcutaneous injection. The effect on bone growth can only be seen using systemic treatment. The reference does not disclose formulations for topical applications into the inflamed gingival pocket to act as a localised anti-inflammatory agent.

It is known that induction of gingival overgrowth is a major undesired effect of systemic cyclosporin in transplant patients (Journal of Periodontology, Vol. 82(10), 2011, (Becerik, Sema et al), "Gingival crevicular fluid osteocalcin, N-terminal telopeptides, and calprotectin levels in cyclosporin A-induced gingival overgrowth", pages 1490-1497). The side effect of gingival overgrowth is not unique to cyclosporin, other compound classes associated with gingival hyperplasia are anticonvulsants and calcium channel blockers, neither of which has anti-inflammatory activity. Gingival hyperplasia associated with all these medications consists of an excess deposit of extracellular matrix and is fundamentally different from physiological tissue, which consists primarily of cells (e.g. Kataoka et al., "Drug-induced gingival overgrowth—a review", Biol Pharm Bull. 2005 October; 28(10):1817-21).

The undesired side effect of systemic treatment can be overcome by using localised topical formulations. Ongoing gingival inflammation, as seen in periodontitis, is a prerequisite of the onset of gingival overgrowth. Agents inhibiting the inflammatory processes of periodontitis could be expected to antagonise gingival overgrowth (Subramani et al., "The possible potential therapeutic targets for drug induced gingival overgrowth", Mediators Inflamm. 2013). Gingival overgrowth induced by cyclosporin has been shown to be correlated with a certain threshold in cyclosporin blood levels (Webb et al., "Correlation between finger-prick and venous cyclosporin levels: association with gingival overgrowth and hypertrichosis", Pediatr Nephrol. 2007 Dec. 22(12):2111; Thomas et al., "Risk factors in the development of cyclosporine-induced gingival overgrowth", Transplantation. 2000 Feb. 27; 69(4):522-6).

However the topical treatments described herein will slow and/or stop the pathophysiology of chronic inflammation which must precede the physiological healing process, without causing the side effects induced by systemic treatment. It is the onset of the physiological healing process, that initiates the re-growth of physiological tissue, and the tissue which is formed by natural healing is fundamentally different from the overgrowth induced by cyclosporin and other drug classes.

DE 102008062373 describes the use of compounds known to induce gingival hypertrophy to fill the interdental gaps created by tissue erosion in periodontitis. There is no evidence of topical administration of any of the compounds mentioned in this document, nor is there any evidence of localised anti-inflammatory activity.

JPH0597697 describes the provision of an alveolar bone-regenerating agent containing cyclosporin A. The document lists a long list of possible compounds, including many that do not have any anti-inflammatory activity. There is no evidence of topical administration of cyclosporin A, nor is there any evidence of localised anti-inflammatory activity.

WO 03/033010 mentions periodontal disease as one condition among an exhaustive list of inflammatory and auto-immune diseases that can be treated with the compounds of WO 03/033010. This reference does not disclose any evidence supporting the claim that periodontal disease could be treated by cyclosporins. Evidence is given for inhibition of the Nuclear Factor of Activated T cells (NFAT), which is relevant for immunosuppression and for use of inhibitory compounds in transplantation. Furthermore, WO 03/033010 describes activity of compounds in test systems such as mixed lymphocyte reaction, plaque forming cell assay (Mishell-Dutton test), or delayed type hypersensitivity. All these test systems detect inhibitory activity of compounds on T cells (i.e. immunosuppressive activity). As outlined above, the role of cyclophilin in the inflammatory process of periodontitis is fundamentally different from that of immunosuppression.

The difference between immunosuppressive and anti-inflammatory activity is best illustrated by the fact that the well-known compound FK506 (Tacrolimus), is an immunosuppressant acting by a mechanism identical to that of cyclosporin but is not known to have anti-inflammatory activity (see e.g. Mattila et al., "The actions of cyclosporin A and FK506 suggest a novel step in the activation of T lymphocytes", EMBO J. 1990 December; 9(13):4425-33; Liu J et al., "Calcineurin is a common target of cyclophilin-cyclosporin A and FKBP-FK506 complexes", Cell. 1991 Aug. 23; 66(4):807-15).

WO 03/033010 A teaches that compounds can be administered by parenteral injection in the form of liquid dosage forms, be given by mouth (perorally) in the form of solid dosage forms, or be administered topically to the lung, eye, or vagina. However the document contains no evidence of topical administration of cyclosporin A, nor is there any evidence of localised anti-inflammatory activity.

SUMMARY OF THE INVENTION

According to one aspect of the invention, cyclophilin inhibitors may be used to treat periodontitis. According to another aspect, the cyclophilin inhibitors belong to the chemical classes of cyclosporins, sanglifehrins or cycloundecadepsipeptides. According to another aspect, the cyclophilin inhibitors may be applied locally into the gingival pocket. According to another aspect, the cyclophilin inhibitors may be applied as a micro- or nano-formulations. According to another aspect, the micro- or nano-formulation is mucoadhesive. According to another aspect, the micro- or nano-formulation allows the cyclophilin inhibitors to exhibit activity over a period of several days or weeks. The nano compositions can be formulated with non-ionic surfactants, for example TPGS and/or poloxamer 407. The composition may be applied as liquids, and which form gels in-situ. The in-situ forming system can be a suspension of cyclosporin nanoparticles which is applied into inflamed gingival pockets as a liquid, where it forms a gel upon exposure to physiological conditions. The in-situ forming systems allow the activity of the cyclosporin to be maintained over a period of several days or weeks. The long acting nature of the composition means that the treatment only needs to be applied once or twice in order to be effective.

DETAILED DESCRIPTION

Figure 1:
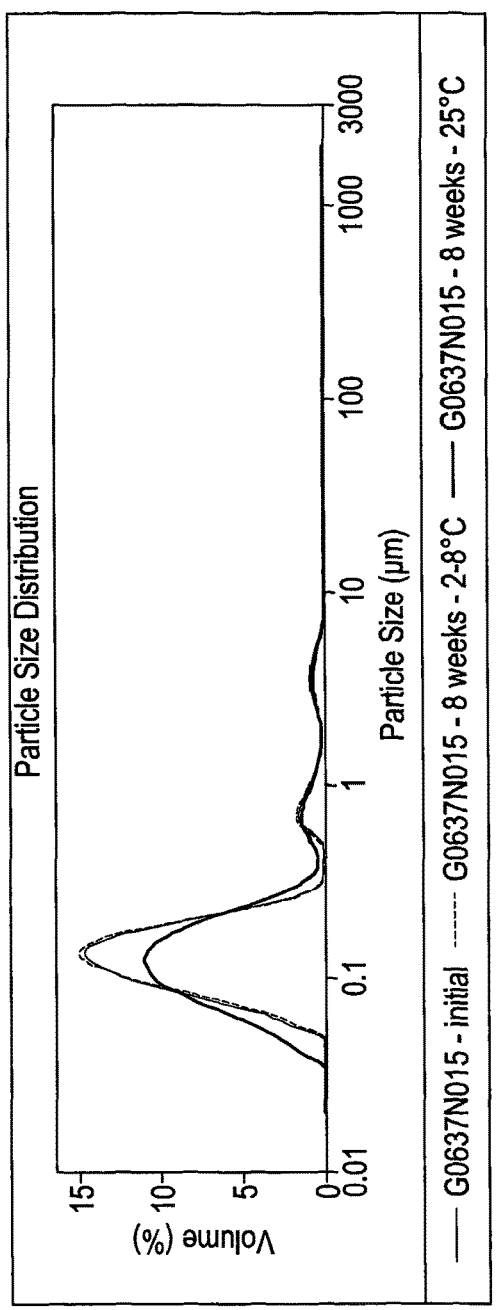
FIG. 1 shows the formulation and stability of a formulation of the active pharmaceutical ingredient (API) Cyclosporin (5%) with 1% TPGS in water. The formulation is stable after 8 weeks at 2-8° C., and shows only a limited amount of aggregation at 25° C.
Figure 2:
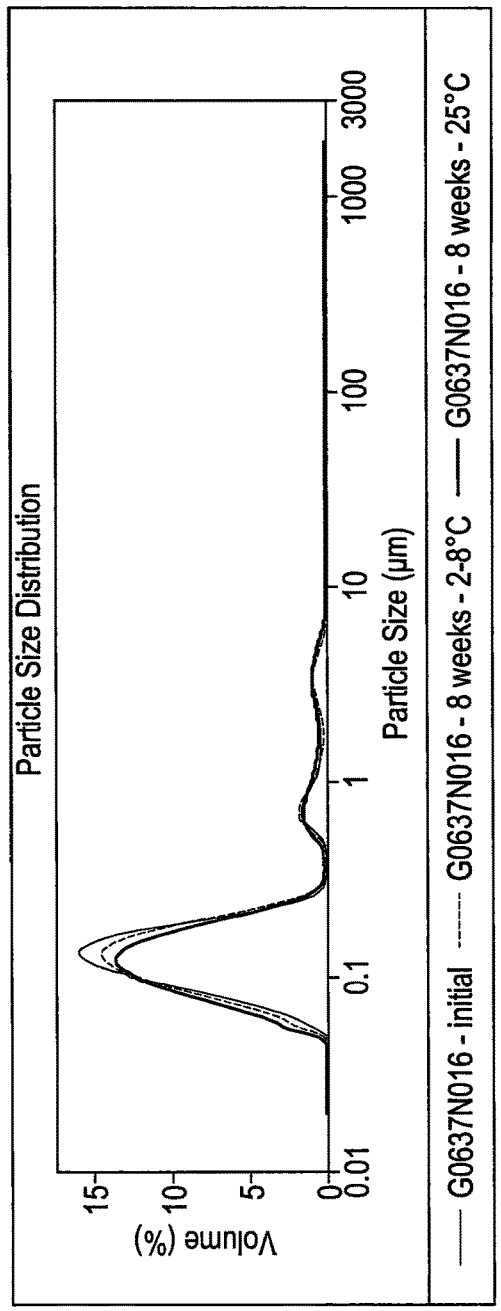
FIG. 2 shows the formulation and stability of a formulation of the active pharmaceutical ingredient (API) Cyclosporin (5%) with 1 TPGS and 1% Poloxamer 407 in water. The formulation is stable after 8 weeks at 2-8° C. The amount of aggregation at 25° C. is reduced by the presence of the poloxamer.
Figure 3:
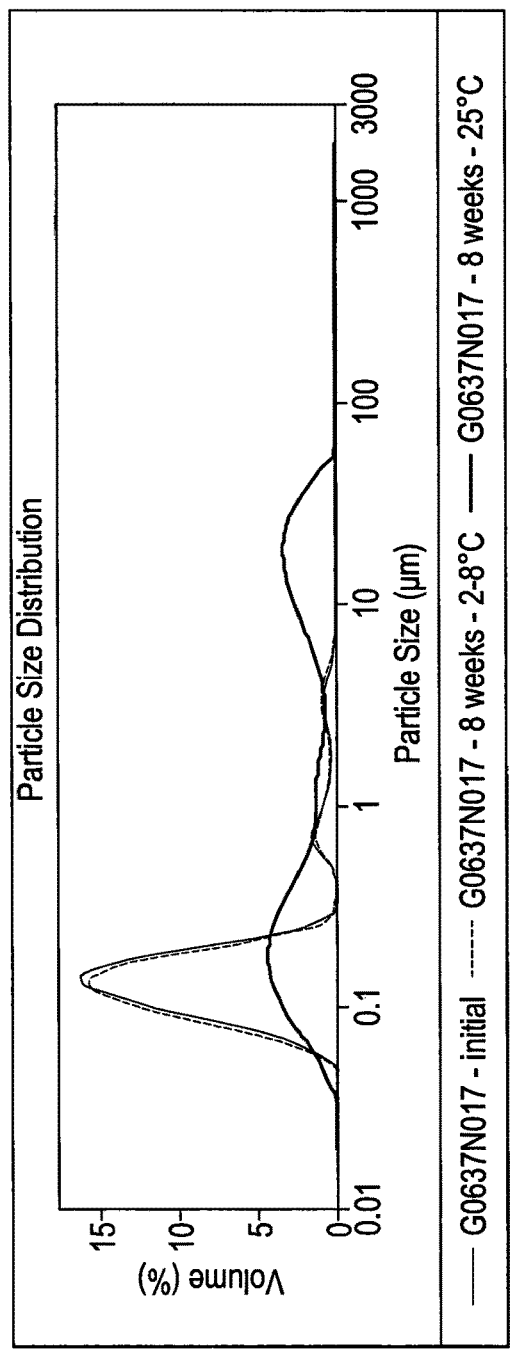
FIG. 3 shows the formulation and stability of a formulation of the active pharmaceutical ingredient (API) Cyclosporin (5%) with 0.8% sodium glycocholate and 2% Poloxamer 407 in water. The formulation is stable after 8 weeks at 2-8° C. The amount of aggregation at 25° C. is substantial. Sodium glycocholate does not appear to confer long term stability to the same level as TPGS.
Figure 4:
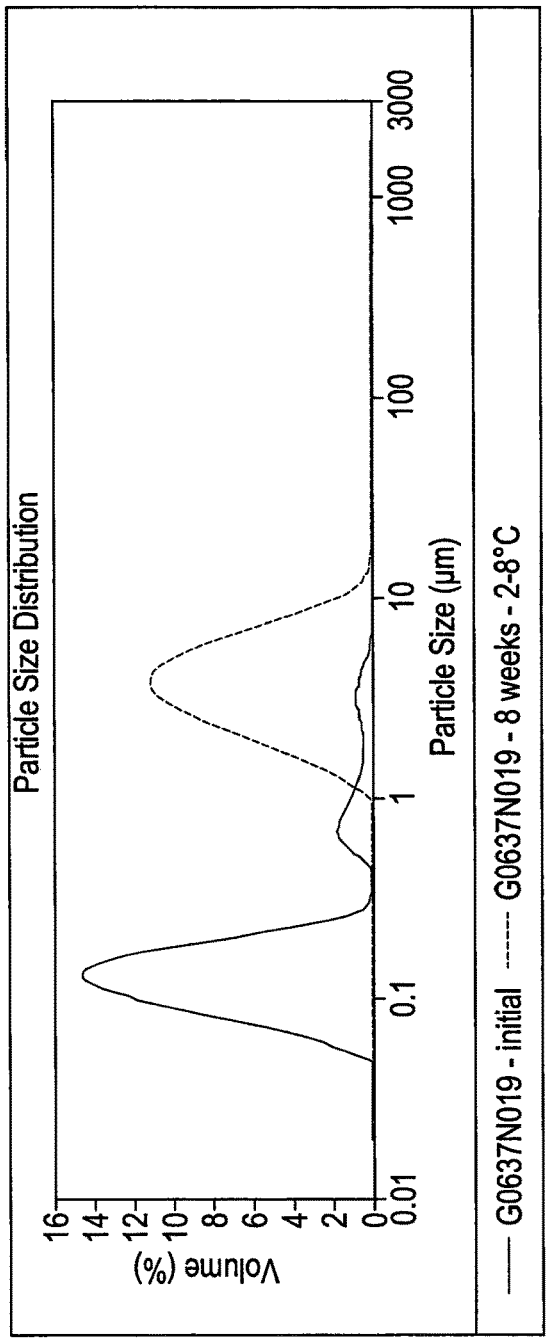
FIG. 4 shows the formulation and stability of a formulation of the active pharmaceutical ingredient (API) Cyclosporin (5%) with 0.02% chitosan and 1% Poloxamer 407 in water. The formulation is not stable, and substantial aggregation of the particles occurs. Chitosan does not appear to confer long term stability to the same level as TPGS.

Described herein is the use of cyclophilin inhibitors in the treatment of periodontal disease. The cyclophilin inhibitor may be a cyclosporin, a sanglifehrin or a cycloundecadepsipeptide. Any compound as described herein may be used in the treatment of periodontal disease and may be formulated into a micro- or nano-formulation. Any compound as described herein may be formulated with a mucoadhesive. Any compound as described herein may be formulated into a micro- or nano-formulation for use as an in-situ forming gel. The micro- or nano-formulation allows the cyclophilin inhibitors to exhibit activity over a period of several days or weeks. The nano compositions can be formulated with non-ionic surfactants, for example TPGS and/or poloxamer 407. The composition may be applied as liquids, and which form gels in-situ. The in-situ forming system can be a suspension of cyclosporin nanoparticles which is applied into inflamed gingival pockets as a liquid, where it forms a gel upon exposure to physiological conditions. The in-situ forming systems allow the activity of the cyclosporin to be maintained over a period of several days or weeks. The long acting nature of the composition means that the treatment only needs to be applied once or twice in order to be effective.

The first cycloundecadepsipeptide to be identified to be a potent inhibitor of cyclophilins has the structure shown in formula A.

formula A

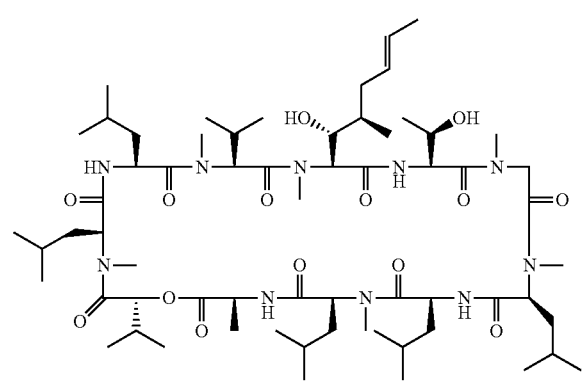

In accordance with WO 2011/141891, this compound can also be described as Cyclo-(MeBmt-Thre-Sar-MeLeu-Leu-MeLeu-Ala-D-Hiv-MeLeu-Leu-MeVal). Compounds of this family can generally be designated as

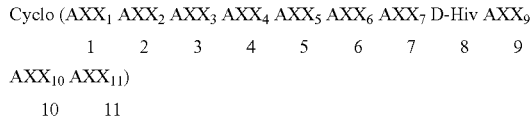

In which $AXX_1$ is N-methyl-(4R)-4-but-2E-en-1-yl-4-methyl-(L)-threonine, and D-Hiv is (D)-2-hydroxyisovalerianic acid.

The compound of formula A may be used in the treatment of periodontal disease or may be formulated into a micro- or nano-formulation as described herein.

More recently, new cycloundecadepsipeptides which retain their ability to bind cyclophilins but with significantly reduced immunosuppressive properties have been disclosed (WO2010/052559 A1). This application claims the use of certain cycloundecadepsipeptides as compounds for treating viral infections, notably by Hepatitis C. The application does not describe the use in the treatment of periodontal disease or the formulation of micro or nanoparticles. Any compound described in WO2010052559 is within the scope of the invention herein. The compounds for use in the treatment of periodontal disease therefore include compounds which can generally be designated as

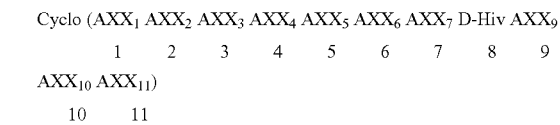

In which $AXX_1$ is MeBmt, 4-fluoro-MeBmt, dihydro-MeBmt, 8-hydroxy-MeBmt, O-acetyl-MeBmt;
$AXX_2$ is Abu, Val, Thr, Thr(OMe), Thr(OAc), Thr(OCOCH$_2$CH$_2$CH$_2$OH), Nva, 5-hydroxy-Nva (Hnv);
$AXX_3$ is D-MeAla, D-3-fluoro-MeAla, D-MeSer, D-MeSer(OAc), D-MeSer(OCH$_2$CH$_2$OH), D-MeSer(OCH$_2$CH$_2$NEt$_2$), D-MeAsp(OMe);
$AXX_4$ is MeLeu, MeIle, MeMet, MeVal, MeThr, MeThr(OAc), MeAla, EtVal, EtIle, EtPhe, EtTyr, EtThr(OAc), MeThr(OAc), MeTyr, MeTyr(OAc), MeTyr(OMe), MePhe, MeMet(Ox) wherein the sulphur atom of methionine is sulphoxide or sulphone;
$AXX_5$ is Leu, Val, Ile, Gly, Abu;
$AXX_6$ is MeAla, Sar, MeLeu;
$AXX_7$ is Gly, Ala;
D-Hiv is (D)-2-hydroxyisovalerianic acid;
$AXX_9$ is MeLeu;
$AXX_{10}$ is Leu; and
$AXX_{11}$ is MeVal.

A cyclophilin inhibitor according to the present invention wherein the inhibitor is a cycloundecadepsipeptide can be designated as

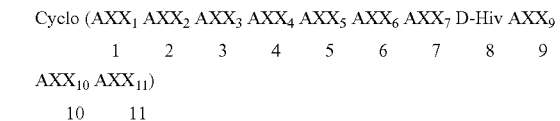

In which $AXX_1$ is MeBmt, 4-fluoro-MeBmt, dihydro-MeBmt, 8-hydroxy-MeBmt, O-acetyl-MeBmt or $AXX_1$ contains a nitrogen atom in the side chain;
$AXX_2$ is Abu, Val, Thr, Thr(OMe), Thr(OAc), Thr(OCOCH$_2$CH$_2$CH$_2$OH) or an alternative threonine ester or threonine-O-alkyl or substituted O-alkyl moiety, Nva, 5-hydroxy-Nva (Hnv) or a moiety of type C(=O)CH$_3$ or C(=N—Y)CH$_3$ where Y is OH, NH$_2$ or O- or N-alkyl or substituted alkyl versions thereof;
$AXX_3$ is optionally substituted alkylene, D-MeAla, D-3-fluoro-MeAla, D-MeSer, D-MeSer(OAc), D-MeSer(OCH$_2$CH$_2$OH), D-MeSer(OCH$_2$CH$_2$NEt$_2$), D-MeAsp(OMe) or a D-amino acid with a side chain selected from hydrogen, alkyl, substituted alkyl, alkoxy, substituted alkoxy, alkylthio or substituted alkylthio;
$AXX_4$ is MeLeu, MeIle, MeMet, MeVal, MeThr, MeThr(OAc), MeAla, EtVal, EtIle, EtPhe, EtTyr, EtThr(OAc), MeThr(OAc), MeTyr, MeTyr(OAc), MeTyr(OMe), MePhe, MeMet(Ox) wherein the sulphur atom of methionine is sulphoxide or sulphone;
$AXX_5$ is Leu, Val, Ile, Gly, Abu;
$AXX_6$ is MeAla, Sar, MeLeu;
$AXX_7$ is Gly, Ala;
D-Hiv is (D)-2-hydroxyisovalerianic acid;

AXX$_9$ is MeLeu;
AXX$_{10}$ is Leu; and
AXX$_{11}$ is MeVal.

Where AXX$_1$ contains a nitrogen atom, the cyclophilin inhibitor may be a cycloundecadepsipeptide having the formula (1);

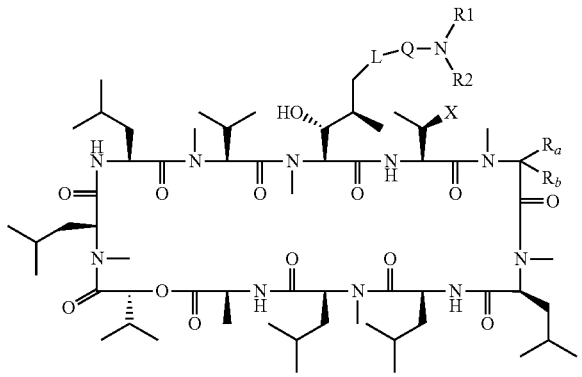

or a pharmaceutically acceptable salt, tautomer or N-oxide thereof, wherein

L represents an optionally substituted, optionally partially unsaturated chain of 1-6 carbon atoms with optional additional heteroatoms atoms in the chain, and may be optionally branched and optionally linked to R$_1$ to form a ring structure containing one or more nitrogen atoms, Q represents a primary, secondary or tertiary covalent bond, a carbonyl group and optionally a linking group to R1, R1 and R2 may be absent or independently represent H, alkyl, substituted alkyl, —COR$_3$, —CO$_2$R$_3$, —OR$_4$, —NR$_4$R$_5$, CONR$_4$R$_5$, —C(=NR$_6$)NR$_4$R$_5$, —C(=NR$_6$)OR$_3$ and optionally R1 and R2 may together with the nitrogen atom to which they are attached form a 4-7 membered aryl, cycloalkyl or heterocyclic ring which may be further fused or optionally substituted, R3 represents alkyl, substituted alkyl, cycloalkyl, optionally substituted aryl or optionally substituted heteroaryl, R4 and R5 independently represent H, alkyl, substituted alkyl, cycloalkyl, optionally substituted aryl or optionally substituted heteroaryl and optionally R4 and R5 may together with the nitrogen atom to which they are attached form a 4-7 membered aryl, cycloalkyl or heterocyclic ring which may be further fused or optionally substituted, R6 represents H, alkyl, substituted alkyl, cycloalkyl, optionally substituted aryl or optionally substituted heteroaryl, X represents OH, OC(=O)-alkyl, OC(=O)-substituted alkyl, O-alkyl, O-substituted alkyl, carbonyl (=O) or imine (=N—Y) where Y is —OR$_4$ or —NR$_4$R$_5$, R$_a$ represents hydrogen, alkyl, substituted alkyl, alkoxy, substituted alkoxy, alkylthio, substituted alkylthio or optionally substituted alkylene, and R$_b$ represents hydrogen or is absent.

The group L-Q-NR1R2 may comprise a primary, secondary or tertiary amino group attached via an optionally substituted alkyl linker.

The group L-Q-NR1R2 may comprise a primary or secondary amide, urea, amidine, guanidine or carbamate group attached via an optionally substituted alkyl linker. Q may be a carbonyl group such that amide may be of orientation —C(=O)N as well as —NC(=O).

The group L-Q-NR1R2 may comprise a C=N double bond moiety, for example C=N—OH, C=N—OR, C=N—NH2, C=N—NHR or C=N—NRR.

The group L-Q-NR1R2 may comprise a nitrogen containing heterocyclic ring. The heterocyclic ring may be a 4-7 membered aryl, cycloalkyl or heterocyclic ring which may be further fused or optionally substituted.

Linking moiety L may be 1-6 carbon atoms. L may contain one or more heteroatoms in the chain. L may contain O, N or S atoms interspersed between the carbon atoms. L may contain a branch point. L may contain one or more double or triple bonds such that L may be partially unsaturated. L may link with R1 or R2 to form a ring containing one or more nitrogen atoms.

Moiety Q may be a covalent bond. Q may be a primary (single) covalent bond, where both R1 and R2 are present. Q may be a secondary covalent (double) bond, where only a single R1 group is present. Q may be a tertiary covalent (triple) bond to make a cyano (CN) group where R1 and R2 are absent. Q may be a carbonyl group such that Q-N is a C(=O)—N amide group. Q may link with R1 or R2 to form a ring containing one or more nitrogen atoms.

Exemplary compounds may be where R1 and R2 are together with the nitrogen atom to which they are attached form a 4-7 membered aryl, cycloalkyl or heterocyclic ring which may be further fused or optionally substituted or optionally partially unsaturated. Exemplary rings include optionally substituted morpholinyl, optionally substituted piperazinyl, optionally substituted oxazepinyl, optionally substituted pyrrolidinyl, optionally substituted piperidinyl, optionally substituted fused pyrrolidinyl, optionally substituted thiomorpholinyl or the S oxides thereof. The ring may be fused to form a bicyclic system.

R1 and R2 may be absent or independently represent H, alkyl, substituted alkyl, —COR$_3$, —CO$_2$R$_3$, —OR$_4$, —NR$_4$R$_5$, CONR$_4$R$_5$, —C(=NR$_6$)NR$_4$R$_5$, —C(=NR$_6$)OR$_3$ and optionally R1 and R2 may together with the nitrogen atom to which they are attached form a 4-7 membered aryl, cycloalkyl or heterocyclic ring which may be further fused or optionally substituted.

R1 and/or R2 may be H. R1 and/or R2 may be alkyl or substituted alkyl. R1 and/or R2 may be methyl or ethyl. R1 or R2 may represent an amide COR$_3$ where R3 represents alkyl, substituted alkyl, cycloalkyl, optionally substituted aryl or optionally substituted heteroaryl. R1 or R2 may represent a carbamate CO$_2$R$_3$ where R3 represents alkyl, substituted alkyl, cycloalkyl, optionally substituted aryl or optionally substituted heteroaryl. R1 or R2 may represent an oxime or hydroxylamine OR$_4$ where R4 represents H, alkyl, substituted alkyl, cycloalkyl, optionally substituted aryl or optionally substituted heteroaryl. R1 or R2 may represent an hydrazone NR$_4$R$_5$ where R4 and R5 independently represent H, alkyl, substituted alkyl, cycloalkyl, optionally substituted aryl or optionally substituted heteroaryl and optionally R4 and R5 may together with the nitrogen atom to which they are attached form a 4-7 membered aryl, cycloalkyl or heterocyclic ring which may be further fused or optionally substituted. R1 or R2 may represent —C(=NR$_6$)NR$_4$R$_5$ or —C(=NR$_6$)OR$_3$ where R3 represents alkyl, substituted alkyl, cycloalkyl, optionally substituted aryl or optionally substituted heteroaryl and R4 and R5 independently represent H, alkyl, substituted alkyl, cycloalkyl, optionally substituted aryl or optionally substituted heteroaryl and optionally R4 and R5 may together with the nitrogen atom to which they are attached form a 4-7 membered aryl, cycloalkyl or heterocyclic ring which may be further fused or optionally substituted and R6 represents H, alkyl, substituted alkyl, cycloalkyl, optionally substituted aryl or optionally substituted heteroaryl.

X represents OH, OC(=O)-alkyl, OC(=O)-substituted alkyl, O-alkyl, O-substituted alkyl, carbonyl (=O) or imine (=N—Y) where Y is —OR$_4$ or —NR$_4$R$_5$. Where X is OH, the amino acid is threonine. The hydroxyl moiety of the threonine can be in the form of an ester or O-alkyl group where the ester or alkyl group is optionally substituted. For example, the amino acid may be Thr(OMe), Thr(OAc), Thr(OCOCH$_2$CH$_2$CH$_2$OH) or an alternative threonine ester or threonine-O-alkyl or substituted O-alkyl moiety. The ester can be in the form OC(=O)-alkyl or OC(=O)-substituted alkyl. X can represent a group of type —OCOR$_3$ or —OCO$_2$R$_3$, where R3 represents alkyl, substituted alkyl, cycloalkyl, optionally substituted aryl or optionally substituted heteroaryl. X can represent a group of type —OR$_4$ where R4 represents H, alkyl, substituted alkyl, cycloalkyl, optionally substituted aryl or optionally substituted heteroaryl. X can be present as a carbonyl group (=O). X can be present as an imine (=N—Y) where Y is —OR$_4$ or —NR$_4$R$_5$ where R4 and R5 independently represent H, alkyl, substituted alkyl, cycloalkyl, optionally substituted aryl or optionally substituted heteroaryl and optionally R4 and R5 may together with the nitrogen atom to which they are attached form a 4-7 membered aryl, cycloalkyl or heterocyclic ring which may be further fused or optionally substituted.

R$_a$ represents hydrogen, alkyl, substituted alkyl, alkoxy, substituted alkoxy, alkylthio, substituted alkylthio or optionally substituted alkylene. Ra includes substituted alkyl groups of type —S—R7, —CH2-S—R7 and the sulfoxide and sulfone analogues thereof where R7 represents H, alkyl or substituted alkyl.

Exemplary groups for Ra include: =CH$_2$, —CH$_2$SH, —CH$_2$—S—(CH$_2$)$_n$N—R$_4$R$_5$, where R4 and R5 independently represent H, alkyl, substituted alkyl, cycloalkyl, optionally substituted aryl or optionally substituted heteroaryl and optionally R4 and R5 may together with the nitrogen atom to which they are attached form a 4-7 membered aryl, cycloalkyl or heterocyclic ring which may be further fused or optionally substituted and n is 1-4, —CH$_2$—S—(CH$_2$)$_n$-aryl where n is 1-4, —CH$_2$—S—(CH$_2$)$_n$-hereroaryl where n is 1-4, —CH$_2$—S—CH$_3$, —CH$_2$—S-cycloalkyl, CH$_2$—S— heterocycloalkyl, —CH$_2$—S—(CH$_2$)$_n$COOR4 where R4 represents H, alkyl, substituted alkyl, cycloalkyl, optionally substituted aryl or optionally substituted heteroaryl and n is 1-4, —CH$_2$—S—(CH$_2$)$_n$—CH=CH$_2$ where n is 1-4, —CH$_2$—S—(CH$_2$)$_n$N—C(=NH)—NH$_2$ where n is 1-4. In each example given above, the sulphur may be oxidised to the sulfoxide or sulfone, and formulas can be represented as —CH$_2$—S(=O)$_m$—(CH$_2$)— where m is 0-2.

Further exemplary groups for Ra can be found in publication US2012/0088734, the contents of which are incorporated herein.

R$_b$ represents hydrogen or is absent where Ra is alkylene.

Exemplary compounds may include a compound of formula 1 wherein L is a chain of 1-6 carbon atoms, Q is a primary covalent bond or a carbonyl group and R1 and R2 are together with the nitrogen atom to which they are attached form a 4-7 membered aryl, cycloalkyl or heterocyclic ring which may be further fused or optionally substituted.

Exemplary compounds may include a compound of formula 1 wherein L is a chain of 1-6 carbon atoms, Q is a primary covalent bond or a carbonyl group and R1 and R2 are together with the nitrogen atom to which they are attached form a 5-7 membered cycloalkyl or heterocyclic ring which may be further fused or optionally substituted.

Exemplary compounds may include a compound of formula 1 wherein the group L-Q-NR1-R2 is selected from —(CH$_2$)$_n$—NR1R2 where n is 1-4 and R1 and R2 may independently represent H, alkyl, substituted alkyl or may together with the nitrogen atom to which they are attached form a 4-7 membered aryl, cycloalkyl or heterocyclic ring which may be further fused or optionally substituted.

Exemplary compounds may include a compound of formula 1 wherein the group L-Q-NR1-R2 is selected from —(CH$_2$)$_n$—S—(CH$_2$)$_m$—NR1R2 where n is 1-4, m is 1-4 and R1 and R2 may independently represent H, alkyl, substituted alkyl or may together with the nitrogen atom to which they are attached form a 4-7 membered aryl, cycloalkyl or heterocyclic ring which may be further fused or optionally substituted.

Exemplary compounds may include a compound of formula 1 wherein the group L-Q-NR1-R2 is selected from —(CH$_2$)$_n$—CO—NR1R2 where n is 1-4 and R1 and R2 may independently represent H, alkyl, substituted alkyl or may together with the nitrogen atom to which they are attached form a 4-7 membered aryl, cycloalkyl or heterocyclic ring which may be further fused or optionally substituted.

Exemplary compounds may include a compound of formula 1 wherein the group L-Q-NR1-R2 is selected from —(CH$_2$)$_n$—S—(CH$_2$)$_m$—CO—NR1R2 where n is 1-4, m is 1-4 and R1 and R2 may independently represent H, alkyl, substituted alkyl or may together with the nitrogen atom to which they are attached form a 4-7 membered aryl, cycloalkyl or heterocyclic ring which may be further fused or optionally substituted.

Exemplary structures for —NR1R2 include

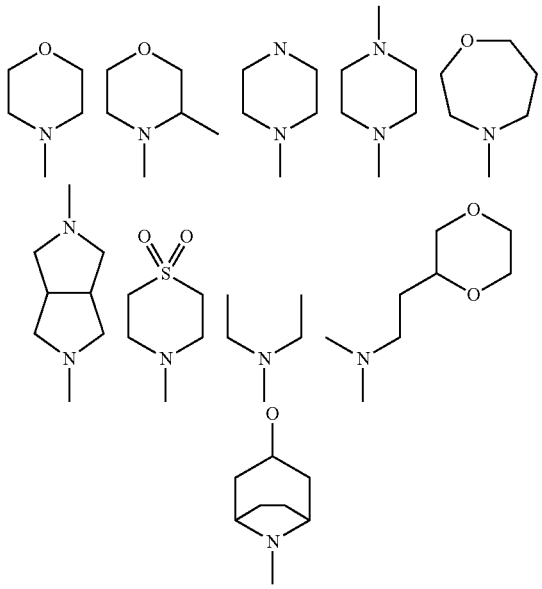

Exemplary compounds include a compound of formula 1 wherein L is a C1-6 alkyl group with 0-1 heteroatom substituents, Q is a primary covalent bond and R1 and R2 are independently H, alkyl or substituted alkyl groups.

Exemplary compounds include a compound of formula 1 wherein L or Q is linked to R$_1$ to form a ring structure containing one or more nitrogen atoms.

Exemplary compounds may include a compound of formula 1 wherein the group L-Q-NR1-R2 is selected from —(CH$_2$)$_n$—NR1R2 where n is 1-4, R1 is H or alkyl, and R2 represents —COR$_3$, —CO$_2$R$_3$, —CONR$_4$R$_5$, —C(=NR$_6$)NR$_4$R$_5$ or —C(=NR$_6$)OR$_3$ where R3 represents alkyl, substituted alkyl, cycloalkyl, optionally substituted aryl or optionally substituted heteroaryl, R4 and R5 independently represent H, alkyl, substituted alkyl, cycloalkyl, optionally substituted aryl or optionally substituted heteroaryl and optionally R4 and R5 may together with the nitrogen atom to which they are attached form a 4-7 membered aryl, cycloalkyl or heterocyclic ring which may be further fused or optionally substituted, and R6 represents H, alkyl, substituted alkyl, cycloalkyl, optionally substituted aryl or optionally substituted heteroaryl.

Exemplary compounds may include a compound of formula 1 wherein the group L-Q-NR1-R2 is selected from —(CH$_2$)$_n$—S—(CH$_2$)$_m$—NR1R2 where n is 1-4, m is 1-4, R1 is H or alkyl, and R2 represents —COR$_3$, —CO$_2$R$_3$, —CONR$_4$R$_5$, —C(=NR$_6$)NR$_4$R$_5$, or —C(=NR$_6$)OR$_3$ where R3 represents alkyl, substituted alkyl, cycloalkyl, optionally substituted aryl or optionally substituted heteroaryl, R4 and R5 independently represent H, alkyl, substituted alkyl, cycloalkyl, optionally substituted aryl, or optionally substituted heteroaryl and optionally R4 and R5 may together with the nitrogen atom to which they are attached form a 4-7 membered aryl, cycloalkyl or heterocyclic ring which may be further fused or optionally substituted, and R6 represents H, alkyl, substituted alkyl, cycloalkyl, optionally substituted aryl or optionally substituted heteroaryl.

Exemplary structures for N—COR$_3$, —CO$_2$R$_3$, —CONR$_4$R$_5$, —C(=NR$_6$)NR$_4$R$_5$ or —C(=NR$_6$)OR$_3$ include:

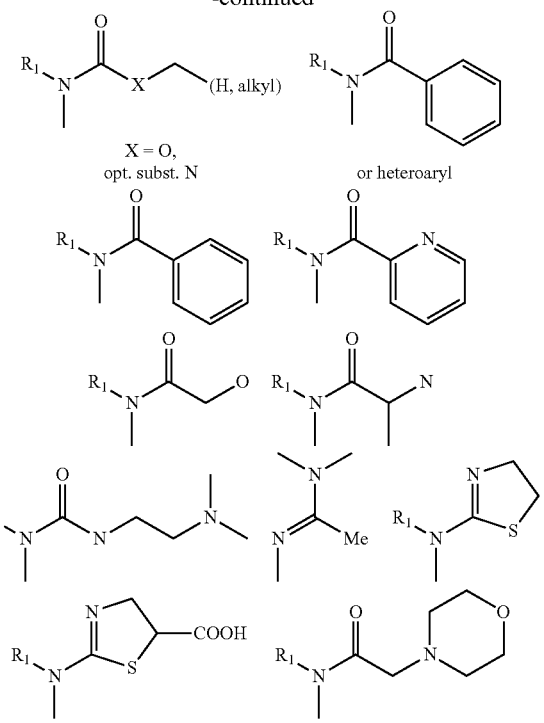

where the arrows indicated positions which can be further substituted. Groups may include

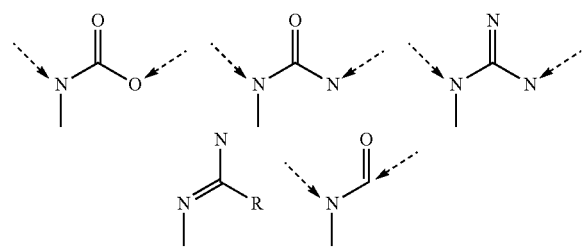

x = N, O, S
opt. substit if N dashed line = saturated or unsaturated carbon chain, monocyclic or polycyclic

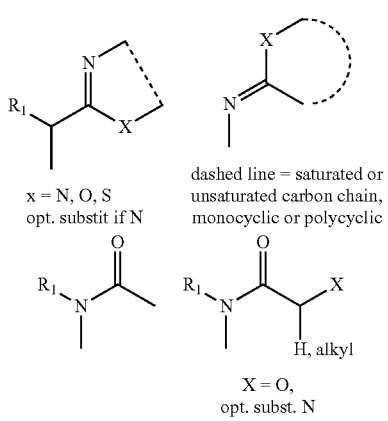

H, alkyl

X = O,
opt. subst. N

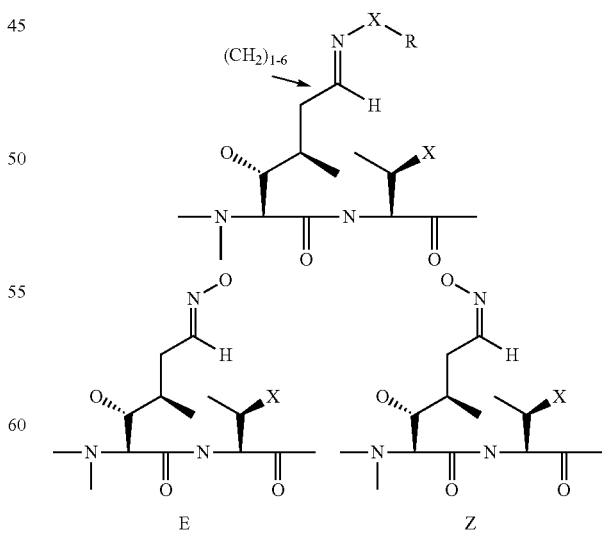

Exemplary compounds include a compound of formula 1 wherein Q is a secondary covalent bond, R1 is absent and R2 is —OR$_4$ or —NR$_4$R$_5$, where R4 and R5 independently represent H, alkyl, substituted alkyl, cycloalkyl, optionally substituted aryl or optionally substituted heteroaryl and optionally R4 and R5 may together with the nitrogen atom to which they are attached form a 4-7 membered aryl, cycloalkyl or heterocyclic ring which may be further fused or optionally substituted.

Exemplary compounds include those shown below. In the diagram below, the L-Q-NR1-R2 group is depicted from the cyclic peptide ring.

all derivatives of this series can have Z and E configuration; only one (E) is shown below

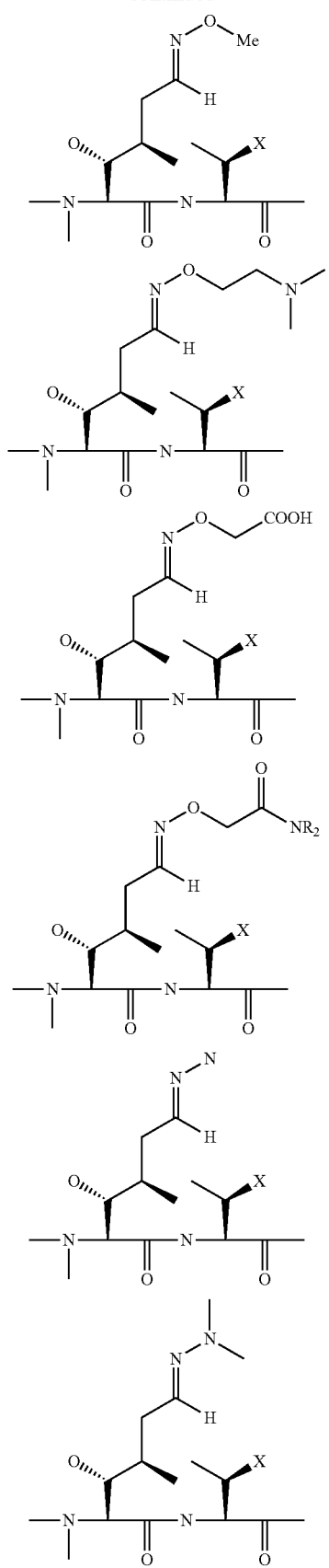
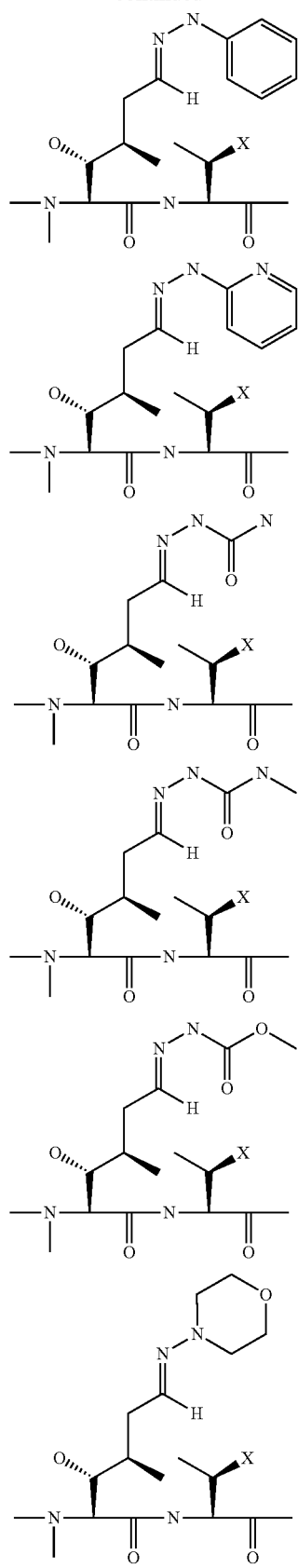

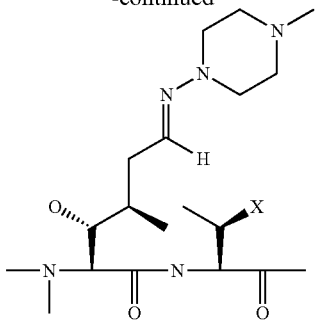
Exemplary amide structures of type CONR1R2 include
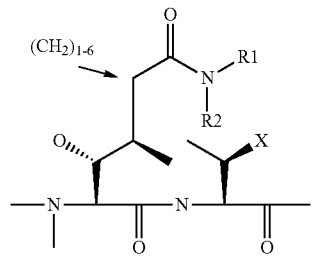
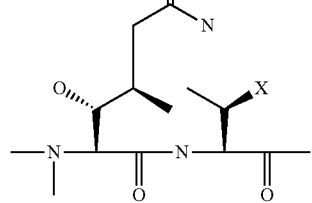
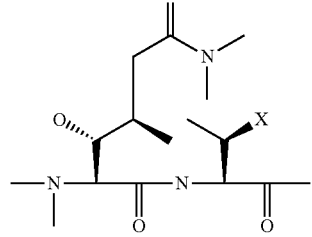
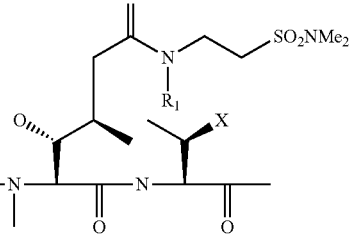
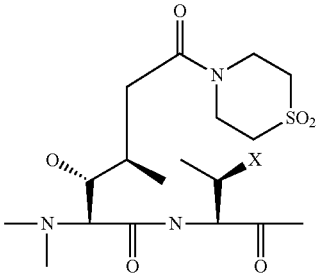
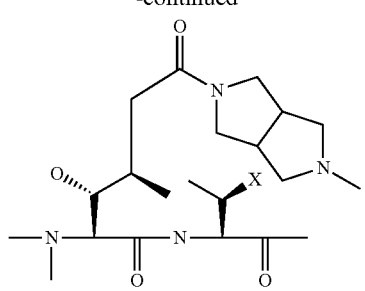
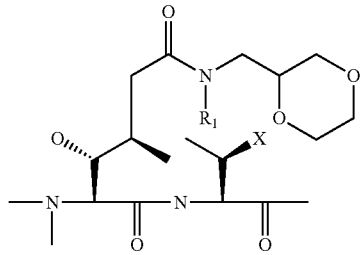
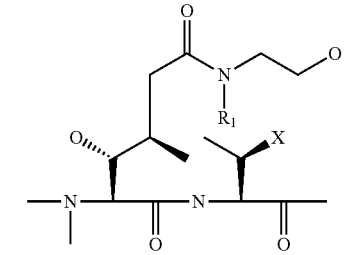
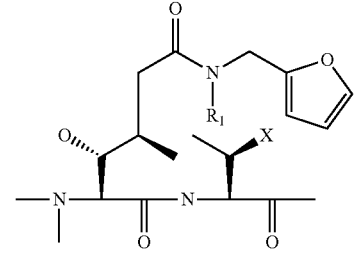
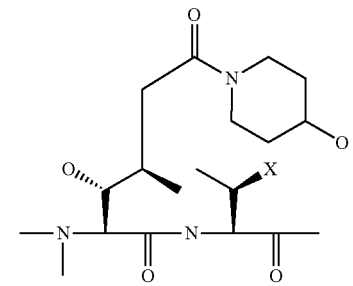
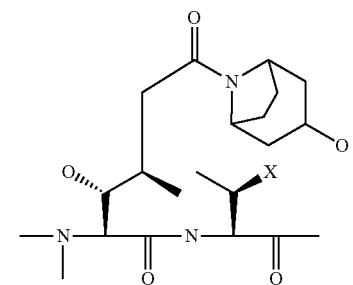

17
-continued
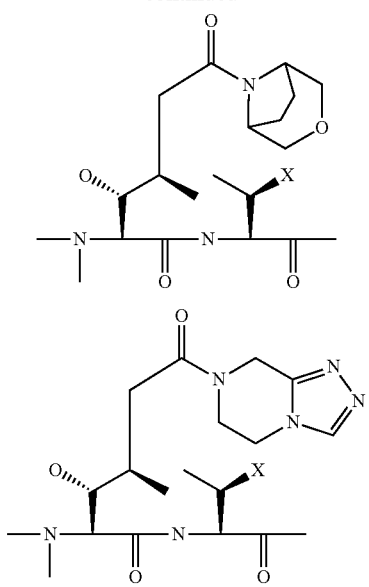
Examples of structures where L or Q are linked to R1 include:
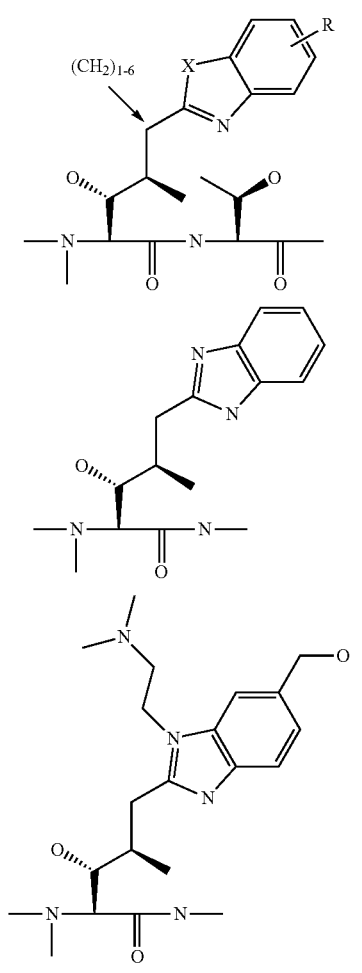
18
-continued
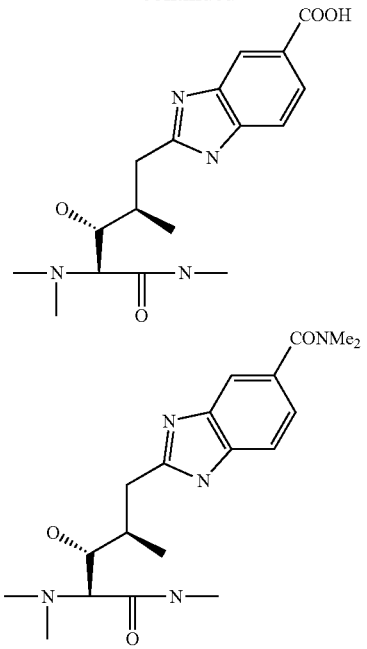
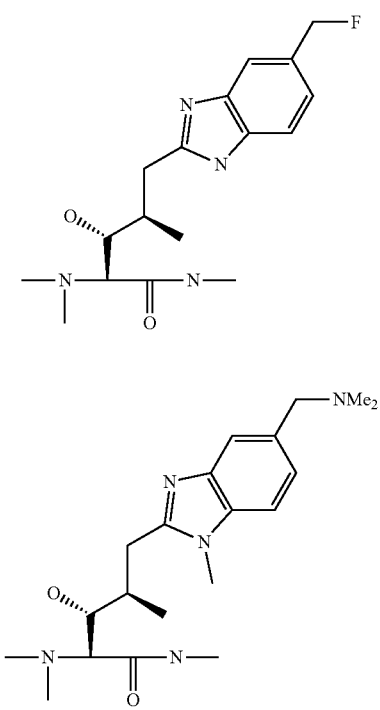

-continued
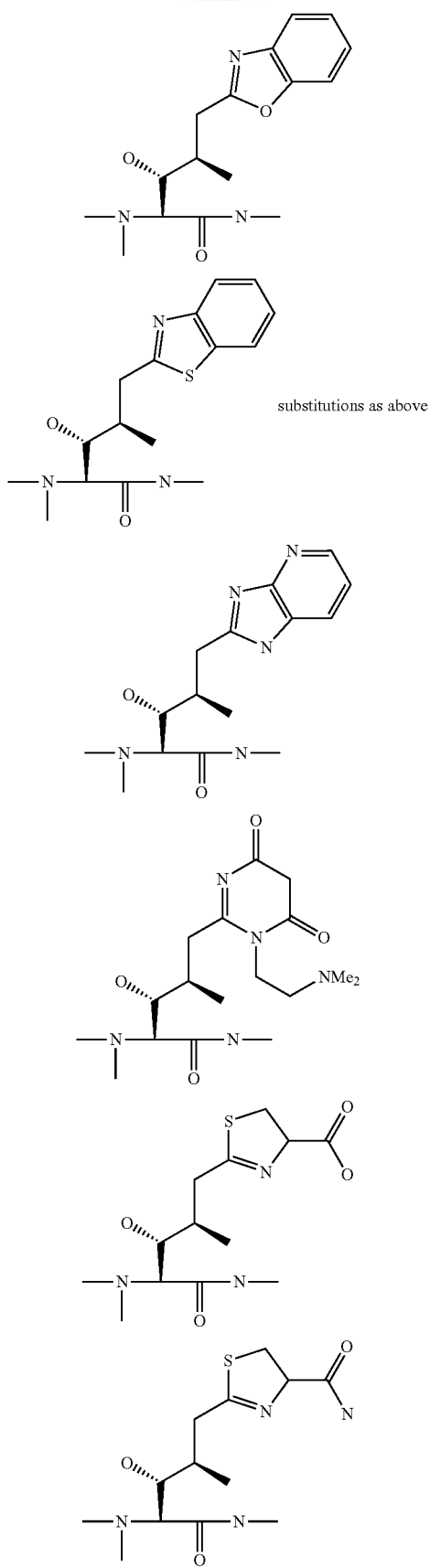
substitutions as above
-continued
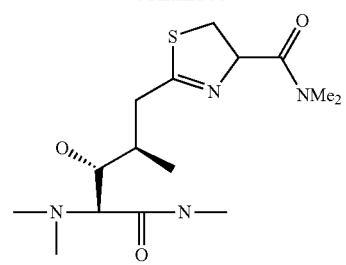
Where R is one or more optional substituents on the aromatic ring.
Alternative structures are
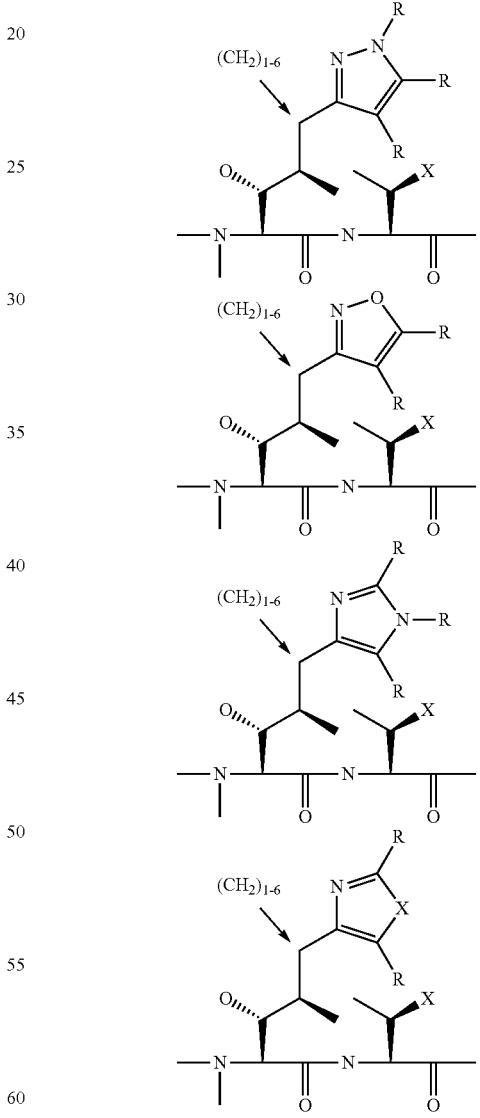
X = O or S
Where R is independently H, alkyl or substituted alkyl.
Alternatively the cyclophilin inhibitor may be a sanglifehrin, or an analogue thereof.

Alternatively, the cyclophilin inhibitor may be a cyclosporin, or a cyclosporin analogue which can be designated as a compound having the formula (2);

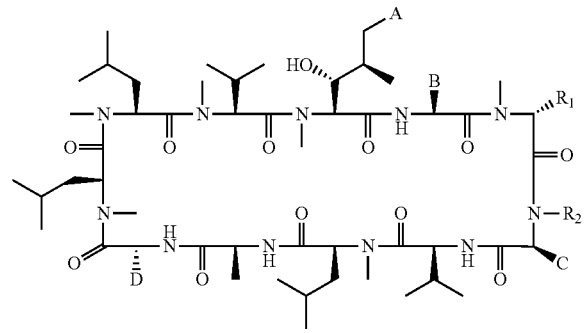

or a pharmaceutically acceptable salt thereof wherein A is —CH=CHR, —CH=CH—CH=CHR or —CH$_2$CH$_2$R, wherein R is —CH$_3$, —CH$_2$SH, —CH$_2$S—C$_n$ wherein n is 1, 2, 3, 4, 5 or 6, —(CH$_2$)$_m$COOR$_a$ wherein m is 0 or 1 and R$_a$ is H or C$_1$-C$_6$ alkyl;

B is methyl, ethyl, 1-hydroxyethyl, isopropyl or n-propyl;

C is isobutyl, 2-hydroxyisobutyl, isopropyl or 1-methylpropyl;

D is —CH$_3$, —CH$_2$OH or —CH$_2$OCH$_2$CH$_2$OH;

R$_1$ is H or a group X—R$_d$ or CR$_b$R$_c$—X—R$_d$ where R$_b$ and R$_c$, which are identical or different, each represents hydrogen or C$_1$-C$_4$ alkyl or together represent C$_3$-C$_7$ cycloalkyl; R$_2$ is methyl or ethyl;

X is bond, sulfur or —S(O)$_n$, wherein n is 1 or 2;

R$_d$ is hydrogen, straight or branched C$_1$-C$_6$ alkyl, straight or branched C$_2$-C$_6$ alkenyl, straight or branched C$_2$-C$_6$ alkynyl, C$_3$-C$_7$ cycloalkyl, C$_4$-C$_7$ heterocyclyl having 1-3 heteroatoms selected from nitrogen, oxygen, and sulfur, aryl, heteroaryl or R$_d$ contains a carboxyl, amino, amido group and wherein R$_d$ may be optionally substituted with one or more groups, identical or different, of C$_1$-C$_6$ alkyl, halogen, hydroxyl, alkoxycarbonyl, carboxyl, cycloalkyl, saturated or partially unsaturated 5-6 member heterocyclyl having 1-3 heteroatoms selected from nitrogen, oxygen, and sulfur, which heterocyclyl is optionally substituted by one or more groups of C$_1$-C$_6$ alkyl, aryl, heteroaryl, amino, monoalkylamino, dialkylamino, amidino, guanidine or urea.

Certain cyclosporin analogues are described in application US20120088734. The new use, or new formulation of any compounds described therein is within the scope of this invention.

The disclosures herein include any pharmaceutically acceptable salts. Where compounds are isomers, all chiral forms and racemates are included. The disclosures include all solvates, hydrates and crystal forms.

The cyclosporin may be cyclosporin A, cyclosporin B, cyclosporin C, cyclosporin D, cyclosporin G, (D)-serine-8-cyclosporin, (D)[O-hydroxyethylserine]-cyclosporin (IMM-125), MeIle-(4)-cyclosporin (NIM-811), Aliosporivir (Debio-025), SCY-635, or SCY-641.

The cyclosporin may be cyclosporin A. Cyclosporin A can be represented by formula:

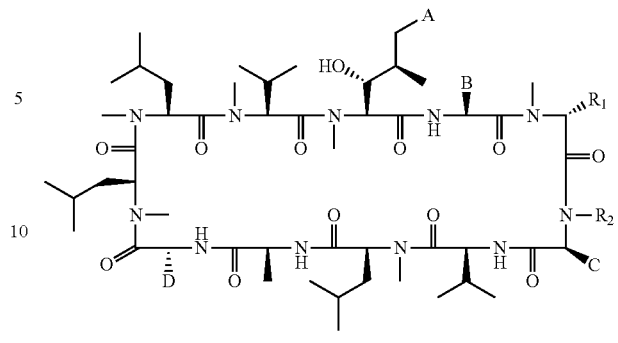

or a pharmaceutically acceptable salt thereof wherein A is —CH=CHR, wherein R is —CH$_3$;

B is ethyl;
C is isobutyl;
D is —CH$_3$;
R$_1$ is H; and
R$_2$ is methyl.

The cyclosporin may be cyclosporin B. Cyclosporin B can be represented by formula:

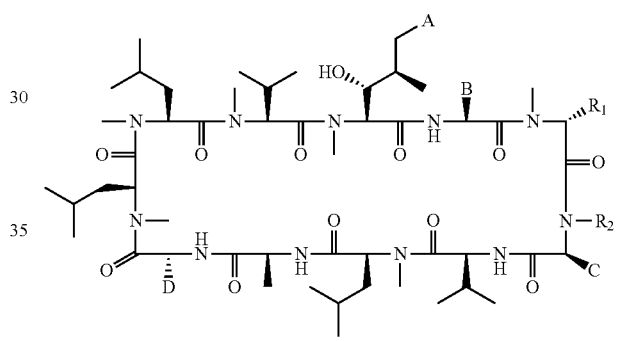

or a pharmaceutically acceptable salt thereof wherein A is —CH=CHR, wherein R is —CH$_3$;

B is methyl;
C is isobutyl;
D is —CH$_3$;
R$_1$ is H; and
R$_2$ is methyl.

The cyclosporin may be cyclosporin C. Cyclosporin C can be represented by formula:

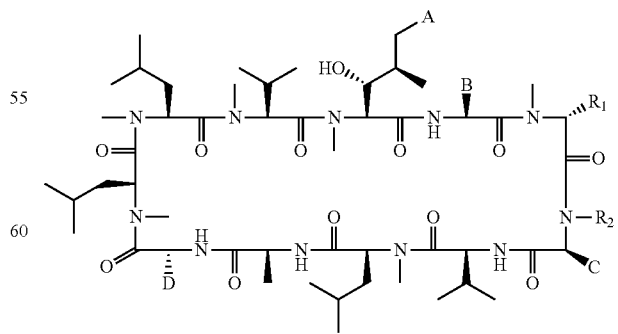

or a pharmaceutically acceptable salt thereof wherein A is —CH=CHR, wherein R is —CH$_3$;

B is 1-hydroxyethyl;

C is isobutyl;

D is —CH₃;

R₁ is H; and

R₂ is methyl.

The cyclosporin may be cyclosporin D. Cyclosporin D can be represented by formula:

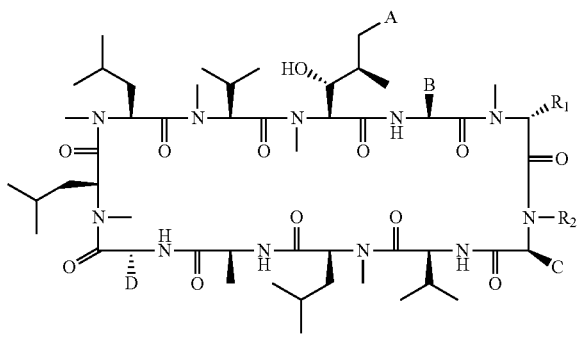

or a pharmaceutically acceptable salt thereof wherein A is —CH=CHR, wherein R is —CH₃;

B is isopropyl;

C is isobutyl;

D is —CH₃;

R₁ is H; and

R₂ is methyl.

The cyclosporin may be cyclosporin G. Cyclosporin G can be represented by formula:

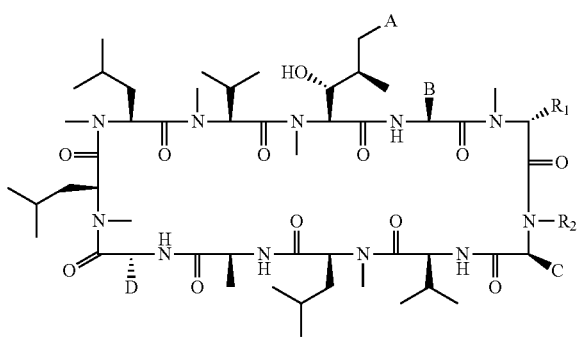

or a pharmaceutically acceptable salt thereof wherein A is —CH=CHR, wherein R is —CH₃;

B is n-propyl;

C is isobutyl;

D is —CH₃;

R₁ is H; and

R₂ is methyl.

The cyclosporin may be (D)-serine-8-cyclosporin. (D)-serine-8-cyclosporin can be represented by formula:

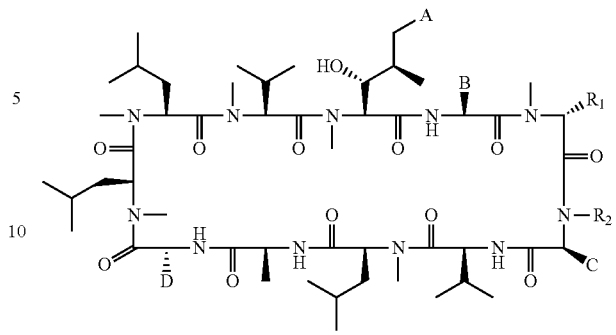

or a pharmaceutically acceptable salt thereof wherein A is —CH=CHR, wherein R is —CH₃;

B is ethyl;

C is isobutyl;

D is —CH₂OH;

R₁ is H; and

R₂ is methyl.

The cyclosporin may be (D)-[O-hydroxyethylserine]-cyclosporin (IMM-125). (D)-[O-hydroxyethylserine]-cyclosporin (IMM-125) can be represented by formula:

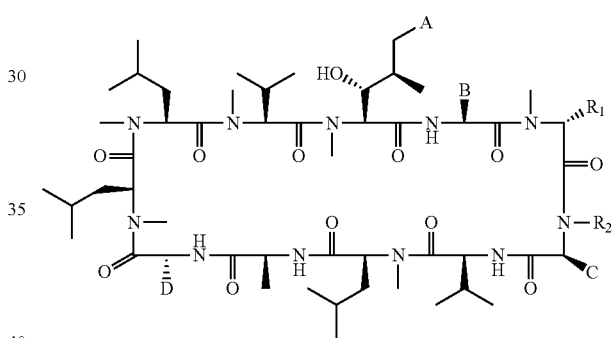

or a pharmaceutically acceptable salt thereof wherein A is —CH=CHR, wherein R is —CH₃;

B is ethyl;

C is isobutyl;

D is —CH₂OCH₂CH₂OH;

R₁ is H; and

R₂ is methyl.

The cyclosporin may be MeIle-(4)-cyclosporin (NIM-811). MeIle-(4)-cyclosporin (NIM-811) can be represented by formula:

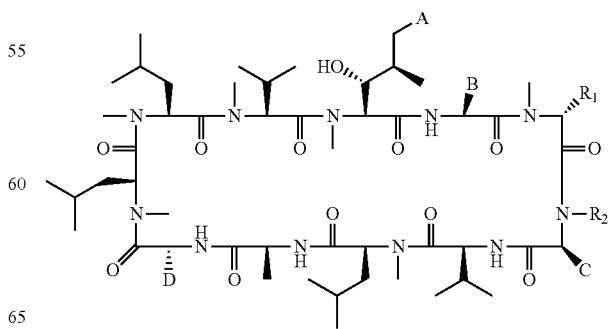

or a pharmaceutically acceptable salt thereof wherein A is
—CH═CHR, wherein R is —CH$_3$;
B is ethyl;
C is 1-methylpropyl;
D is —CH$_3$;
R$_1$ is H; and
R$_2$ is methyl.

The cyclosporin may be Aliosporivir (Debio-025). Aliosporivir (Debio-025) can be represented by formula:

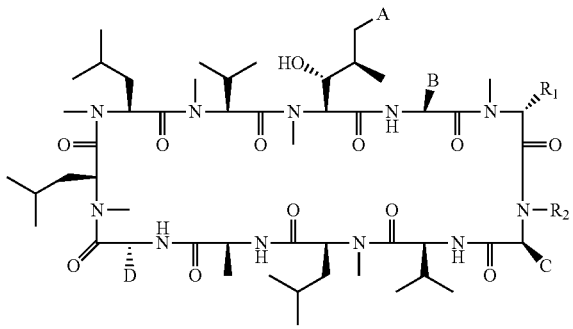

or a pharmaceutically acceptable salt thereof wherein A is
—CH═CHR, wherein R is —CH$_3$;
B is ethyl;
C is isopropyl;
D is —CH$_3$;
R$_1$ is CR$_b$R$_c$—X—R$_d$ where R$_b$ and each represents hydrogen; X is bond, and R$_d$ is hydrogen (i.e. R$_1$ is methyl); and
R$_2$ is ethyl.

The cyclosporin may be SCY-635 or SCY-641. SCY-635 can be represented by formula:

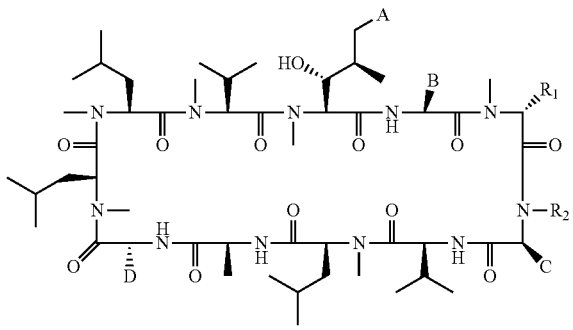

or a pharmaceutically acceptable salt thereof wherein A is
—CH═CHR, wherein R is —CH$_3$;
B is ethyl;
C is 2-hydroxyisobutyl;
D is —CH$_3$;
R$_1$ is X—R$_d$ where X is sulphur and R$_d$ is CH$_2$CH$_2$NMe$_2$
R$_2$ is methyl.

To the extent that any of the compounds described have chiral centres, the present invention extends to all isomers of such compounds, whether in the form of diastereomeric mixtures or or separated diastereomers. The invention described herein relates to all crystal forms, solvates and hydrates of any of the disclosed compounds however so prepared. To the extent that any of the compounds disclosed herein have acid or basic centres such as carboxylates or amino groups, then all salt forms of said compounds are included herein. In the case of pharmaceutical uses, the salt should be seen as being a pharmaceutically acceptable salt.

Pharmaceutically acceptable salts that may be mentioned include acid addition salts and base addition salts. Such salts may be formed by conventional means, for example by reaction of a free acid or a free base form of a compound with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound in the form of a salt with another counter-ion, for example using a suitable ion exchange resin.

Examples of pharmaceutically acceptable salts include acid addition salts derived from mineral acids and organic acids, and salts derived from metals such as sodium, magnesium, or preferably, potassium and calcium or organic bases such as ethanolamine, N,N-dialkylethanolamines, morpholine, etc.

Examples of acid addition salts include acid addition salts formed with acetic, 2,2-dichloroacetic, citric, lactic, mandelic, glycolic, adipic, alginic, aryl sulfonic acids (e.g., benzenesulfonic, naphthalene-2-sulfonic, naphthalene-1,5-disulfonic and p-toluenesulfonic), ascorbic (e.g. L-ascorbic), L-aspartic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, gluconic (e.g. D-gluconic), glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic and (±)-DL-lactic), lactobionic, maleic, malic (e.g. (−)-L-malic), (±)-DL-mandelic, metaphosphoric, methanesulfonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulfuric, tannic, tartaric (e.g. (+)-L-tartaric), thiocyanic, undecylenic and valeric acids.

Particular examples of salts are salts derived from mineral acids such as hydrochloric, hydrobromic, phosphoric, metaphosphoric, nitric and sulfuric acids; from organic acids, such as tartaric, acetic, citric, malic, lactic, fumaric, benzoic, glycolic, gluconic, succinic, arylsulfonic acids; and from metals such as sodium, magnesium, or preferably, potassium and calcium.

Also encompassed are any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography. The solvates can be stoichiometric or non-stoichiometric solvates. Particular solvates may be hydrates, and examples of hydrates include hemihydrates, monohydrates and dihydrates.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

Preparation of Suspensions

Included herein are novel formulations of the cyclophilin inhibitors. The preparation of certain micro-formulations of cyclosporin is disclosed in application U.S. Pat. No. 8,202,540. U.S. Pat. No. 8,202,540 does not disclose the co-formulation of mucoadhesives and cyclophilin inhibitors. Furthermore, U.S. Pat. No. 8,202,540 does not disclose the preparation of in situ gel forming systems of cyclosporin. The use of these cyclophilin inhibitor formulations in the treatment of periodontal disease is disclosed herein. In order to prolong bioavailability in the oral cavity, the cyclophilin inhibitor may be formulated into a suspension of microparticles or nanoparticles. Microparticles have a size range in the micrometer scale, and nanoparticles have a size range in the nanometer scale. Suitable formulations may have a particle size of around 1 μm. For example, at least 50% of the particles in the formulation may be less than 1 μm in size. At least 50% of the particles may be of size 200 nm to 1 μm in size.

The cyclophilin inhibitor may be dispersed as a powder by stirring into a mechanically agitated dispersion medium to prepare a pre-suspension. For the mechanical agitation a variety of devices can be used, such as e.g. a propeller mixer, dissolver discs, or rotor-stator mixers. The dispersion medium may be water containing a suitable surfactant or non-aqueous liquid to act as a stabilising substance. Alternatively, the dispersion medium may be a non aqueous liquid. All liquids except water can be used as dispersion media, such as polyols (e.g. ethylene glycol, propylene glycol, glycerol), polyethylene glycols, medium chain triglycerides, vegetable oils, liquid hydrocarbons, or alcohols. Water may be admixed to the dispersion media up to amounts of 1-20%, preferably 1-10%.

The cyclophilin inhibitor, in amorphous or crystalline form, may be dispersed as a powder by stirring into a mechanically agitated dispersion medium to prepare a foam-free pre-suspension. For the mechanical agitation a variety of devices can be used, such as e.g. a propeller mixer, dissolver discs, or rotor-stator mixers. As dispersion medium water containing stabilizers can be used.

To stabilise the suspension, one or more stabilising substances can be added. Examples of stabilising substances are poloxamers and poloxamines (polyoxyethylene-polyoxypropylene block copolymers), polysorbates, ethoxylated fatty alcohols or fatty acids. A particularly preferred stabilising substance is Vitamin E TPGS (d-alpha tocopheryl polyethylene glycol 1000 succinate). Stabilising substances can also be charged, such as phosphatidyl glycerol, lecithins of various origins, phospholipids, sphingolipids, cholates, or amino acids; amphoteric ionic surfactants such as CHAPSO (3-[(3-Cholamidopropyl)dimethylammonio]-2-hydroxy-1-propanesulfonate), CHAPS (3-[(3-cholamidopropyl)dimethylammonio]-1-propanesulfonate); or cationic surfactants, in particular substances used as preservatives such as cetylpyridinium chloride, benzalkonium chloride, chlorhexidine, or methyl-benzethonium chloride.

To achieve mucoadhesive properties of the formulation, a number of bioadhesive polymers can be used. Bioadhesive polymers have numerous hydrophilic groups such as hydroxyl, carboxyl, amide, phosphate or sulfate groups. These hydrophilic groups cause the polymer to swell in water and attach to mucosal surfaces by a combination of hydrogen bonding, electrostatic and hydrophobic interactions. Examples of such polymers are lectins, carbopol (polyacrylic acid), chitosan, hydroxyethyl cellulose, hydroxypropyl cellulose, or sodium carboxymethyl cellulose.

The pre-suspension can be further dispersed in a high-pressure homogeniser such as a French press, piston-gap homogeniser, jet stream homogeniser, bead mills, rotor-stator systems, or ultrasound-based systems. Homogenisation can be carried out at pressures between 100 and 2,000 bar using one, several or many cycles.

The micro or nanoparticles can be characterised in terms of particle size by laser diffractometry and photon correlation (PCS) spectroscopy. A particle size stated as D50% of 1 μM means that 50% of the particles have a diameter of 1 μM.

Any of the cyclophilin inhibitor compounds disclosed herein may be suspended as microparticle or nanoparticle formulations. Disclosed herein are formulations of cyclosporin and mucoadhesives as microparticles or nanoparticles. Exemplary compounds may include cyclosporin A, cyclosporin B, cyclosporin C, cyclosporin D, cyclosporin G, (D)-serine-8-cyclosporin, (D)[O-hydroxyethylserine]-cyclosporin (IMM-125), MeIle-(4)-cyclosporin (NIM-811), Aliosporivir (Debio-025), SCY-635, or SCY-641.

Preferred active agents include cyclosporin A (CyA). Suitable formulations of CyA include those with a neutral surfactant TPGS (Tocopheryl Polyethylene Glycol Succinate). Further surfactants may include poloxamers, for example Poloxamer 407 (Pluronic F127). The composition may include poloxamer 407 and TPGS. Suitable compositions may include CyA (5%), TPGS (1%) and Poloxamer 407 (1%). The cyclosporin used can be amorphous or crystalline, and can be micronised before suspension. The use of micronised agents avoids the need for precipitation of the drug from organic solvents, thus avoiding organic solvent residues in the final composition. The use of crystalline CyA avoids any problems with insoluble polymorphs and leads to controlled drug release rates.

The micro or nanosuspensions can be further formulated. The viscosity of the formulation can be increased to form a gel. For example a high concentration (15-20%) of poloxamer can be used. The gel can be thermosensitive such that it is liquid at room temperature, but can solidify at 37° C. or similar physiological conditions. Suitable gels may contain 15-20% poloxamer 407. Suitable gels may contain 17% poloxamer 407. Alternatively suitable gels may contain hydroxypropyl methylcellulose (HPMC).

The formulation may contain a preservative such as an anti-microbial formulation. The preservative may be chlorhexidine gluconate.

Chemical Definitions

Amino

Amino means $NH_2$ and substituted amino. Substituted amino means $NHR$ or $NR^2R^3$ where $R^2$ and $R^3$ are independent substituents or where $NR^2R^3$ forms an optionally substituted 4 to 7 membered non-aromatic heterocyclic ring optionally containing a second heteroatom ring member selected from O, N and S and oxidised forms thereof Exemplary substituted amino groups include $NMe_2$, $NEt_2$, piperidinyl, piperazinyl, morpholino, N-cyclohexyl, where the rings may be further substituted.

Alkyl

Alkyl means an aliphatic hydrocarbon group. The alkyl group may be straight or branched or cyclic. "Branched" means that at least one carbon branch point is present in the group. Thus, for example, tert-butyl and isopropyl are both branched groups. The alkyl group may be a lower alkyl group. "Lower alkyl" means an alkyl group, straight or branched, having 1 to about 6 carbon atoms, e.g. 2, 3, 4, 5 or 6 carbon atoms.

Exemplary alkyl groups include methyl, ethyl, n-propyl, i-propyl, n-butyl, t-butyl, s-butyl, n-pentyl, 2-pentyl, 3-pentyl, n-hexyl, 2-hexyl, 3-hexyl, n-heptyl, 2-heptyl, 3-heptyl, 4-heptyl, 2-methyl-but-1-yl, 2-methyl-but-3-yl, 2-methyl-pent-1-yl, 2-methyl-pent-3-yl.

The alkyl group may be optionally substituted, e.g. as exemplified below.

The term alkyl also includes aliphatic hydrocarbon groups such as alkenyl, and alkylidene and cycloalkyl, cycloalkylidene, heterocycloalkyl and heterocycloalkylidene groups, which may be further substituted.

Alkenyl

Alkenyl means an unsaturated aliphatic hydrocarbon group. The unsaturation may include one or more double bond, one or more triple bond or any combination thereof. The alkenyl group may be straight or branched. "Branched" means that at least one carbon branch point is present in the group. Any double bond may, independently of any other double bond in the group, be in either the (E) or the (Z) configuration.

The alkenyl group may be a lower alkenyl group. "Lower alkenyl" means an alkenyl group, straight or branched, having 2 to 6 carbon atoms, e.g. 2, 3, 4, 5 or 6 carbon atoms.

Exemplary alkenyl groups include ethenyl, n-propenyl, i-propenyl, but-1-en-1-yl, but-2-en-1-yl, but-3-en-1-yl, pent-1-en-1-yl, pent-2-en-1-yl, pent-3-en-1-yl, pent-4-en-1-yl, pent-1-en-2-yl, pent-2-en-2-yl, pent-3-en-2-yl, pent-4-en-2-yl, pent-1-en-3-yl, pent-2-en-3-yl, pentadien-1-yl, pentadien-2-yl, pentadien-3-yl. Where alternative (E) and (Z) forms are possible, each is to be considered as individually identified.

The alkenyl group may be optionally substituted, e.g. as exemplified below. Alkenyl includes cyano.

Alkylidene

Alkylidene means any alkyl or alkenyl group linked to the remainder of the molecule via a double bond. The definitions and illustrations provided herein for alkyl and alkenyl groups apply with appropriate modification also to alkylidene groups.

Alkylthio

Alkylthio means any alkyl group containing a sulfur atom in the carbon chain. The sulphur atom may be in the form of a thioether (C—S—C), a sulfoxide (C—S(=O)—C) or sulfone (C—S(=O)$_2$—C). Alkylthio groups may be further substituted. Alkylthio groups include CH$_2$—S—R where R is a further alkyl, cycloalkyl or substituted alkyl group.

Cycloalkyl

Cycloalkyl means a cyclic non-aromatic hydrocarbon group. The cycloalkyl group may include non-aromatic unsaturation. The cycloalkyl group may have 3 to 6 carbon atoms, e.g. 3, 4, 5 or 6 carbon atoms. Exemplary cycloalkyl groups include cyclopropyl, cyclobutyl, cyclopentyl, cyclohexyl, cyclopentenyl, cyclohexenyl.

The cycloalkyl group may be optionally substituted, as defined below, e.g. as exemplified below. Exemplary substituted cycloalkyl groups include mono- or poly-alkyl-substituted cycloalkyl groups such as 1-methylcyclopropyl, 1-methylcyclobutyl, 1-methylcyclopentyl, 1-methylcyclohexyl, 2-methylcyclopropyl, 2-methylcyclobutyl, 2-methylcyclopentyl, 2-methylcyclohexyl, 1,2-dimethylcyclohexyl or 1,3-dimethylcyclohexyl.

Cycloalkylidene Group

Cycloalkylidene means any cycloalkyl group linked to the remainder of the molecule via a double bond. The definitions and illustrations provided herein for cycloalkyl groups apply with appropriate modification also to cycloalkylidene groups.

Heterocycloalkyl

Heterocycloalkyl group means a non-aromatic cyclic group which contains one or more heteroatoms in the ring. The heterocycloalkyl group may contain O, N or S atoms. The heterocycloalkyl group may be fully saturated or partially unsaturated. The heterocycloalkyl group is typically monocyclic or bicyclic, and more usually is monocyclic.

Exemplary heterocycloalkyl groups include azetidinyl, pyrrolidinyl, piperidinyl, azepinyl, diazepinyl, dihydrofuranyl (e.g. 2,3-dihydrofuranyl, 2,5-dihydrofuranyl), 4,5-dihydro-1H-maleimido, dioxolanyl, 2-imidazolinyl, imidazolidinyl, isoxazolidinyl, morpholinyl, oxazolidinyl, piperazinyl, pyrrolidinonyl, 2-pyrrolinyl, 3-pyrrolinyl, sulfolanyl, 3-sulfolenyl, tetrahydrofuranyl, thiomorpholinyl, dihydropyranyl (e.g. 3,4-dihydropyranyl, 3,6-dihydropyranyl), dioxanyl, hexahydropyrimidinyl, 2-pyrazolinyl, pyrazolidinyl, pyridazinyl, 4H-quinolizinyl, quinuclinyl, tetrahydropyranyl, 3,4,5,6-tetrahydropyridinyl, 1,2,3,4-tetrahydropyrimidinyl, 3,4,5,6-tetrahydropyrimidinyl, tetrahydrothiophenyl, tetramethylenesulfoxide, thiazolidinyl, 1,3,5-triazinanyl, 1,2,4-triazinanyl, hydantoinyl, and the like. The point of attachment may be via any atom of the ring system.

Heterocycloalkylidene Group

Heterocycloalkylidene means any heterocycloalkyl group linked to the remainder of the molecule via a double bond. The definitions and illustrations provided herein for heterocycloalkyl groups apply with appropriate modification also to heterocycloalkylidene groups.

Optionally Substituted

"Optionally substituted" as applied to any group means that the said group may if desired be substituted with one or more substituents, which may be the same or different. 'Optionally substituted alkyl' includes both 'alkyl' and 'substituted alkyl'.

Examples of suitable substituents for "substituted" and "optionally substituted" moieties include halo (fluoro, chloro, bromo or iodo), $C_{1-6}$ alkyl, $C_{3-6}$ cycloalkyl, hydroxy, $C_{1-6}$ alkoxy, cyano, amino, nitro, $C_{1-6}$ alkylamino, $C_{2-6}$ alkenylamino, di-$C_{1-6}$ alkylamino, $C_{1-6}$ acylamino, di-$C_{1-6}$ acylamino, $C_{1-6}$ aryl, $C_{1-6}$ arylamino, $C_{1-6}$ aroylamino, benzylamino, $C_{1-6}$ arylamido, carboxy, $C_{1-6}$ alkoxycarbonyl or ($C_{1-6}$ aryl)($C_{1-10}$ alkoxy)carbonyl, carbamoyl, mono-$C_{1-6}$ carbamoyl, di-$C_{1-6}$ carbamoyl or any of the above in which a hydrocarbyl moiety is itself substituted by halo, cyano, hydroxy, $C_{1-2}$ alkoxy, amino, nitro, carbamoyl, carboxy or $C_{1-2}$ alkoxycarbonyl. In groups containing an oxygen atom such as hydroxy and alkoxy, the oxygen atom can be replaced with sulphur to make groups such as thio (SH) and thio-alkyl (S-alkyl). Optional substituents therefore includes groups such as S-methyl. In thio-alkyl groups, the sulphur atom may be further oxidised to make a sulfoxide or sulfone, and thus optional substituents therefore includes groups such as S(O)-alkyl and S(O)$_2$-alkyl.

Substitution may take the form of double bonds, and may include heteroatoms. Thus an alkyl group with a carbonyl (C=O) instead of a CH$_2$ can be considered a substituted alkyl group.

Substituted groups thus include for example CFH$_2$, CF$_2$H, CF$_3$, CH$_2$NH$_2$, CH$_2$OH, CH$_2$CN, CH$_2$SCH$_3$, CH$_2$OCH$_3$, OMe, OEt, Me, Et, —OCH$_2$O—, CO$_2$Me, C(O)Me, i-Pr, SCF$_3$, SO$_2$Me, NMe$_2$, CONH$_2$, CONMe$_2$ etc. In the case of aryl groups, the substitutions may be in the form of rings from adjacent carbon atoms in the aryl ring, for example cyclic acetals such as O CH$_2$—O.

The term "pharmaceutical composition" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may take the form, for example, of tablets, dragees, powders, elixirs, syrups, liquid preparations including suspensions, sprays, inhalants, tablets, lozenges, emulsions, solutions, cachets, granules, capsules and suppositories, as well as liquid preparations for injections, including liposome preparations.

The dosages may be varied depending upon the requirements of the patient, the severity of the condition being treated, and the compound being employed. Determination of the proper dosage for a particular situation is within the skill of the art. Generally, treatment is initiated with the smaller dosages which are less than the optimum dose of the compound. Thereafter the dosage is increased by small increments until the optimum effect under the circumstances is reached. For convenience, the total daily dosage may be divided and administered in portions during the day if desired.

The magnitude of an effective dose of a compound will, of course, vary with the nature of the severity of the condition to be treated and with the particular compound and its route of administration. The selection of appropriate dosages is within the ability of one of ordinary skill in this art, without undue burden. In general, the daily dose range may be from about 0.1 mg to about 100 mg per kg body weight of a human and non-human animal, preferably from about 1 mg to about 50 mg per kg of body weight of a human and non-human animal, and most preferably from about 3 mg to about 30 mg per kg of body weight of a human and non-human animal.

Biological Applications

The cyclophilin inhibitors of the invention may be used to treat periodontitis. As described herein, the invention includes the use of cyclosporins, sanglifehrins or cycloundecadepsipeptides for the treatment, or the manufacture of medicaments for use in the treatment of periodontitis or periodontal disease. The cyclophilin inhibitors may be prepared as compositions with mucoadhesives. Disclosed herein are pharmaceutical formulations containing a mucoadhesive and one or more agents selected from cyclosporins, sanglifehrins or cycloundecadepsipeptides.

The cyclophilin inhibitors or pharmaceutical formulations may be applied locally into the gingival pocket. The cyclophilin inhibitors or formulations may be applied as a micro- or nano-formulations. According to another aspect, the micro- or nano-formulation is or contains a mucoadhesive. The micro- or nano-formulation may be optimised to release the cyclophilin inhibitor over a period of several days or weeks. The cyclophilin inhibitors may be used in combination with other agents. Two or more cyclophilin inhibitors may be used together, or the composition may consist of a cyclophilin inhibitor and a further agent, which may be anti-bacterial or immunosuppressant.

The cyclophilin inhibitors or pharmaceutical formulations may be administered orally or by injection into the gums. The cyclophilin inhibitors or pharmaceutical formulations may be administered via a mouthwash containing the active ingredients. The cyclophilin inhibitors or pharmaceutical formulations may be administered as liquid formulations which become gels in-situ.

The cyclophilin inhibitors or pharmaceutical formulations may be used in humans or in veterinary products. The cyclophilin inhibitors or pharmaceutical formulations may be used in canines to treat canine periodontitis.

Methods for the Preparation of Compounds of the Invention

Step 1: Production of Compound 1; Cyclo-(MeBmt-Thre-Sar-MeLeu-Leu-MeLeu-Ala-D-Hiv-MeLeu-Leu-MeVal). by fermentation of strain NRRL-18230.

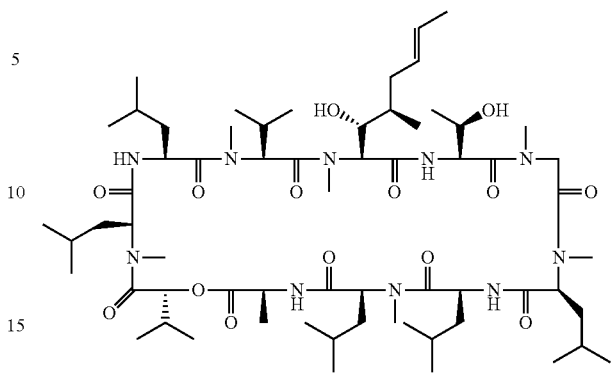

compound 1

Cylindrotrichum sp. NRRL-18230 was sourced from the culture collection at the Agricultural Research Service, US Dept of Agriculture, US, and cultured on malt yeast agar (MYA: 2% malt extract, 0.4% yeast extract, 2% agar in deionised water) at 22° C. Starting material was generated by suspending ten 0.5 cm$^2$ plugs taken from the growing edges of a mature agar plate culture in sterile distilled water (10 ml) containing glass beads (2.5-3.5 mm diameter, 5 ml) and shaking vigorously to cause homogenisation. A seed culture was generated by aseptically inoculating each of three 250 ml conical flasks containing 100 ml malt yeast broth (MYB: 2% malt extract and 0.4% yeast extract in deionised water at native pH) with 2 ml of the starting material and culturing at 22° C. and 150 rpm on a rotating shaker. After 11 days the mycelial pellets from the first seed stage were macerated with glass beads in distilled water and a second seed stage was generated by inoculating each of fifteen 250 ml conical flasks containing 100 ml MYB medium with 10% v/v of the macerated material and culturing at 22° C. and 150 rpm. After a further 14 days, a production stage was initiated by inoculating each of six 5 L Erlenmeyer flasks containing 2.5 L MYB medium with 250 ml of macerated material from mycelia pellets produced from the second seed stage. The cultures were grown at 100 rpm and 22° C. and harvested after 14 days when titres of cyclo-(MeBmt-Thre-Sar-MeLeu-Leu-MeLeu-Ala-D-Hiv-MeLeu-Leu-MeVal). had reached a plateaux, as determined by sampling and analysing by reverse phase HPLC. The harvest biomass was collected by centrifugation at 3000 rpm for 15 minutes using a Beckman J6B Centrifuge. The resulting pellet was extracted by homogenising the biomass with portions of ethyl acetate (3×2.5 L) followed by intermittent stirring over several hours to allow extraction to occur. This process was similarly repeated with methanol (2×1.5 L). The ethyl acetate and methanol extracts were separately concentrated by rotary evaporation. The ethyl acetate extract was defatted by dissolving in acetonitrile (300 ml) and extracting with n-hexane (2×300 ml). The combined hexane layers were back-extracted with acetonitrile (300 ml) and then the acetonitrile layers were combined and dried to yield 1.2 g of acetonitrile-soluble material. The methanol extract was similarly defatted to yield 2.7 g of acetonitrile-soluble material. The acetonitrile-soluble samples from the ethyl acetate and methanol extracts were dissolved and combined in 1:1 n-hexane:ethyl acetate (10 ml) and purified by column chromatography on silica gel (35-70 µm, column: ø 8 cm×16 cm) eluting initially with n-hexane:ethyl acetate (1:1) followed by ethyl acetate and then ethyl acetate-methanol (98:2 followed by 96:4), with all mobile phases containing 0.1% formic acid. Fractions found to contain only the compound of interest, as determined by analysis using reversed phase HPLC with evaporative light scattering detection, were combined and concentrated in vacuo to yield pure Cyclo-(MeBmt-Thre-Sar-MeLeu-Leu-MeLeu-Ala-D-Hiv-MeLeu-Leu-MeVal). (1.248 g).

Step 2: Preparation of compound 2; cyclo-[(3R,4R,5S)-4-(hydroxy)-3-methyl-5-(methylamino)-1-N-morpholino-hexanoic acid-Thre-Sar-MeLeu-Leu-MeLeu-Ala-D-Hiv-MeLeu-Leu-MeVal]

compound 2

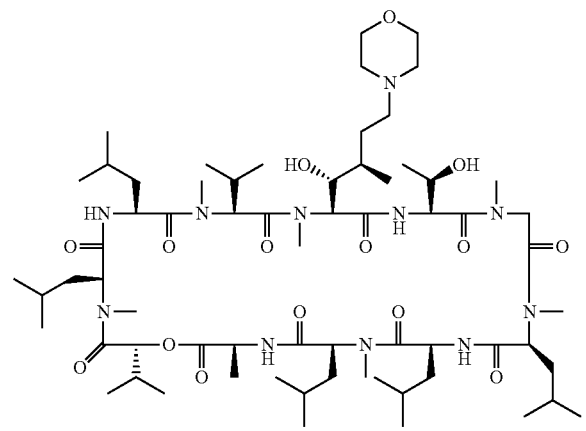

Step 2a: Preparation of cyclo-{[(3R,4R,5 S)-4-(hydroxy)-3-methyl-5-(methylamino)-1-oxo-hexanoic acid-Thre-Sar-MeLeu-Leu-MeLeu-Ala-D-Hiv-MeLeu-Leu-MeVal]}

The product obtained in step 1 (0.124 g, 0.1 mmol) was dissolved in dry dichloromethane (16 ml) and added to a 3-neck flask equipped with a glass inlet tube (for nitrogen/ozone addition) with an outlet connected to a Dreschler bottle containing 2 M potassium iodide solution. The reaction mixture was cooled to −78° C. using a solid $CO_2$/acetone bath under a nitrogen atmosphere. When the temperature of the reaction vessel had stabilised, ozone was bubbled through the reaction mixture until it became a pale blue colour (approx. 3-5 minutes). The ozone supply was removed and dry nitrogen gas was then bubbled through the reaction mixture until the blue colour disappeared. Dimethylsulphide (0.038 ml) was then added, and the reaction mixture was allowed to warm to room temperature over 3 hours. After this time, the reaction mixture was washed with brine then dried ($Na_2SO_4$), filtered and evaporated under reduced pressure to yield the crude title compound which was used in the next step without isolation.

ESMS MNa+ 1257.1, MK+ 1273.3

Step 2b: Preparation of Compound 2; cyclo-[(3R,4R,5S)-4-(hydroxy)-3-methyl-5-(methylamino)-1-N-morpholino-hexanoic acid-Thre-Sar-MeLeu-Leu-MeLeu-Ala-D-Hiv-MeLeu-Leu-MeVal]

To a stirred solution of the compound obtained in step 2a (0.123 g, 0.1 mmol) in dry dichloromethane (10 ml) was added morpholine (0.044 ml, 0.5 mmol), sodium triacetoxyborohydride (0.089 g, 0.5 mmol) and the reaction mixture was stirred at room temperature for 18 h. After this time, additional amounts of morpholine (0.044 ml, 0.5 mmol) and sodium triacetoxyborohydride (0.089 g, 0.5 mmol) were added and the reaction mixture was stirred at 40° C. for 4.5 h. After this time, additional amounts of morpholine (0.025 ml, 0.28 mmol) and sodium triacetoxyborohydride (0.089 g, 0.5 mmol) were added and the reaction mixture was stirred at room temperature for a further 23 h. The reaction mixture was diluted with dichloromethane, washed with a saturated aqueous solution of sodium bicarbonate, brine, then the organic phase was dried ($Na_2SO_4$), filtered and evaporated. The residue was purified by SCX chromatography using a solvent gradient of 100% ethanol to 0.21 M trimethylamine in ethanol followed by MPLC chromatography using a solvent gradient of 100% dichloromethane to 92% dichloromethane/8% ethanol to give title compound as a white solid.

ESMS MH+ 1306.6

Compound 2 may be used in the treatment of periodontal disease, or may be formulated into a suspension as described below.

Methods for the Preparation of Suspensions of Cyclosporin

EXAMPLE 1

To a 5% suspension of cyclosporin in glycerol were added under mechanical agitation (rotor-stator mixer, Ultra Turrax T25) 1% of TPGS, 0.01% chlorhexidine, 7% gelatin, and 10% hydroxypropyl cellulose. The resulting pre-dispersion was then homogenised using 3 cycles at 500 bar and 10 cycles at 1,500 bar in a Gaulin Micron Lab40 high pressure homogeniser at room temperature. Particle size analysis showed a D50% of 1.8 µM, a D75% of 4.6 µM and a D95% of 5.6 µM.

EXAMPLE 2

The same experimental protocol as in example 1 but using 20 high pressure homogenisation cycles gave cyclosporin nanoparticles with a D95% of 960 nM.

EXAMPLE 3

The experimental protocol of example 2 but substituting Polyoxamer 407 for TPGS and 20 high pressure homogenisation cycles gave cyclosporin nanoparticles with a D50% of 890 nM and a D95% of 1.7 µM.

General Nanomilling Procedure (Pilot Scale)

The indicated amount of purified water was weighed into a glass beaker of suitable size. Afterwards the listed amounts of surfactant and stabilising polymer were added under magnetic stirring until the components fully dissolved. The described amount of cyclosporin was slowly added under stirring to give an almost homogenous suspension. The suspension was transferred into the milling system (e.g. Netzsch, DeltaVita). The milling system has been previously loaded with milling beads with approx. 0.2 mm diameter. The milling is performed under controlled temperature conditions (<40° C.) over a suitable time (2-5 h) using an appropriate milling speed (2000-3000 rpm).

Characterisation

The isolated nano-suspensions have been measured on particle size distribution (PSD) by static laser diffraction (e.g. Malvern Mastersizer). In addition the stability of the nano-suspensions have been measured after storage at 2-8° C. and 25° C./60% humidity.

Additives to the Nanosuspension

Figure 5:
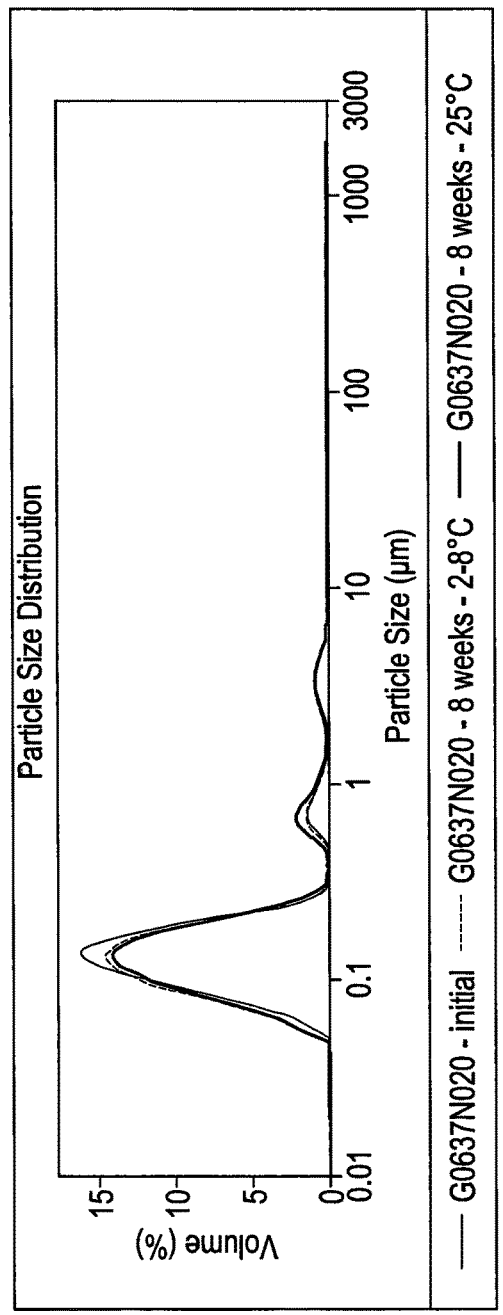
FIG. 5 shows the formulation and stability of a formulation of the active pharmaceutical ingredient (API) Cyclosporin (5%) with 1% TPGS in water. The crystalline cyclosporin is micronized before formulation. Comparison with FIG. 1 shows improved long term stability at 25° C.

The surfactants selected from the neutral surfactants TPGS, cationic system (chitosan) or anionic system (sodium glycocholate). Data using the different surfactants is shown in FIGS. 1-4. FIG. 5 shows the benefits of micronized cyclosporin for particle stability.

In addition, the polymers like the Poloxamer 407 can also be added to the final nanosuspension to increase the gel forming at higher temperatures without any impact on the particles size distribution, as shown in FIG. 6. The stability of the formulation is shown below:

G0637N016 with added Poloxamer 407 to a final concentration of 15% Poloxamer:

| Batch No. | PSD [nm] | PSD Origin NS | PSD initial | PSD 2 weeks 2-8° C. | PSD 2 weeks 25° C. | PSD 4 weeks 2-8° C. | PSD 4 weeks 25° C. |
|---|---|---|---|---|---|---|---|
| G0637N016_Ga | d(10) | 83 | 85 | 81 | 81 | 81 | 81 |
| | d(50) | 135 | 136 | 136 | 136 | 135 | 136 |
| | d(90) | 556 | 526 | 602 | 634 | 609 | 641 |

Preservatives like the Chlorhexidine gluconate can be added without any impact on the nanoparticles in the nanosuspension. The data for this is shown below:
Impact of the addition of Chlorhexidine Gluconate (0.2% CHG) on the Neutral Nanosuspension G0637N016:

| Batch No. | Preservative Batch Code | Quantity | Added amount of 0.2% CHG | PSD [nm] | PSD initial | PSD 4 weeks 2-8° C. | PSD 4 weeks 25° C. |
|---|---|---|---|---|---|---|---|
| G0837N016 | G0637N016_Pa | 15 g | 0.075 g | d(10) | 84 | 85 | 84 |
| | | | | d(50) | 135 | 136 | 127 |
| | | | | d(90) | 518 | 579 | 637 |

The invention claimed is:

1. A topical pharmaceutical composition comprising a suspension of micro-particles or nano-particles in an aqueous solution, wherein the aqueous solution comprises TPGS (Tocopheryl Polyethylene Glycol Succinate) and wherein the micro-particles or nano-particles consist of cyclosporin A wherein cyclosporin A is present in an amount of 5% and TPGS is present in an amount of 1%.

2. The composition according to claim 1 further comprising a poloxamer.

3. The composition according to claim 2 wherein the composition comprises 1% TPGS and 1% Poloxamer 407.

4. The composition according to claim 1 wherein the cyclosporin A is crystalline.

5. The composition according to claim 1 wherein the cyclosporin A is micronized before formulation.

6. The composition according to claim 1 wherein the composition consists of particles where greater than 50% of the particles are less than 1 micrometer in diameter.

7. The composition according to claim 1 further comprising a mucoadhesive.

8. The composition according to claim 7 wherein the mucoadhesive is selected from lectins, carbopol (polyacrylic acid), chitosan, hydroxyethyl cellulose, hydroxypropyl cellulose, or sodium carboxymethyl cellulose.

9. The composition according to claim 1 further comprising an antimicrobial preservative.

10. The composition according to claim 1 formulated to form an in-situ gel.

11. The composition according to claim 10 wherein the composition is formulated with 15-20% poloxamer 407.

12. The composition according to claim 10 wherein the composition is formulated with hydroxypropyl methylcellulose (HPMC).

13. A method of treating periodontal disease in a subject in need thereof, comprising administering an effective amount of the composition of claim 1 to the subject.

14. A method according to claim 13 wherein the disease affects humans or canines.

15. The method according to claim 13 wherein the composition is applied into the gingival pocket.

16. The method according to claim 13 wherein the composition is liquid upon application, but forms a gel in-situ.

* * * * *